United States Patent
Itoh et al.

(10) Patent No.: US 9,829,380 B2
(45) Date of Patent: Nov. 28, 2017

(54) SPECTROSCOPIC APPARATUS

(71) Applicant: Panasonic Intellectual Property Management Co., Ltd., Osaka (JP)

(72) Inventors: Tatsuo Itoh, Osaka (JP); Koichi Kusukame, Nara (JP); Aki Yoneda, Hyogo (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 123 days.

(21) Appl. No.: 14/427,481

(22) PCT Filed: Jun. 20, 2014

(86) PCT No.: PCT/JP2014/003333
§ 371 (c)(1),
(2) Date: Mar. 11, 2015

(87) PCT Pub. No.: WO2015/008435
PCT Pub. Date: Jan. 22, 2015

(65) Prior Publication Data
US 2015/0211928 A1 Jul. 30, 2015

(30) Foreign Application Priority Data

Jul. 17, 2013 (JP) .................................. 2013-148888
Feb. 4, 2014 (JP) .................................. 2014-019552

(51) Int. Cl.
*G01J 4/00* (2006.01)
*G01J 3/46* (2006.01)
(Continued)

(52) U.S. Cl.
CPC .............. *G01J 3/427* (2013.01); *G01J 3/021* (2013.01); *G01J 3/0208* (2013.01);
(Continued)

(58) Field of Classification Search
CPC .... G01N 21/49; G01N 21/53; G01N 15/0205; G01N 15/0227; G01N 21/538;
(Continued)

(56) References Cited

U.S. PATENT DOCUMENTS 6,040,916 A 3/2000 Griesinger
6,263,725 B1 * 7/2001 Garver ................ G01N 1/2035
250/372
(Continued)

FOREIGN PATENT DOCUMENTS

CN 101194828 6/2008
DE 41 33 359 4/1993
(Continued)

OTHER PUBLICATIONS

Extended European Search Report dated Jun. 24, 2016 in corresponding European Application No. 14826966.5.
(Continued)

*Primary Examiner* — Sunghee Y Gray
(74) *Attorney, Agent, or Firm* — Wenderoth, Lind & Ponack, L.L.P.

(57) ABSTRACT

A light radiating portion radiates light with wavelength λ1 having predetermined absorptivity for an object and light with wavelength λ2 having smaller absorptivity for the object than the wavelength λ1, to a target, so as to scan in 2-dimensional directions. A light receiving portion receives scattered lights reflected by the target based on light with wavelength λ1 and light with wavelength λ2. A measuring portion generates information used for detection of the object at the target, based on difference between the two scattered lights with wavelength λ1 and wavelength λ2 received by the light receiving portion. An output portion outputs whether or not the object is present at the target, by 2-dimensional area information, based on scanning by the light radiating portion and information generated by the measuring portion.

22 Claims, 21 Drawing Sheets

(51) Int. Cl.
*G01J 3/427* (2006.01)
*G01N 21/359* (2014.01)
*G01J 3/02* (2006.01)
*G01J 3/433* (2006.01)
*G01J 3/10* (2006.01)
*G01J 3/28* (2006.01)
*G01J 3/32* (2006.01)
*G01J 3/42* (2006.01)
*G01J 3/06* (2006.01)
*G01J 1/42* (2006.01)

(52) U.S. Cl.
CPC ........... *G01J 3/0224* (2013.01); *G01J 3/0237* (2013.01); *G01J 3/0243* (2013.01); *G01J 3/0278* (2013.01); *G01J 3/0289* (2013.01); *G01J 3/10* (2013.01); *G01J 3/2803* (2013.01); *G01J 3/32* (2013.01); *G01J 3/42* (2013.01); *G01J 3/433* (2013.01); *G01N 21/359* (2013.01); *G01J 2001/4242* (2013.01); *G01J 2003/064* (2013.01); *G01J 2003/102* (2013.01); *G01J 2003/104* (2013.01); *G01J 2003/106* (2013.01)

(58) Field of Classification Search
CPC ......... G01N 15/1459; G01N 2201/061; G01N 2201/0633; G01N 21/359; G08B 17/107; G01J 2001/4242; G01J 2003/064; G01J 2003/102; G01J 2003/104; G01J 2003/106; G01J 3/0208; G01J 3/10; G01J 3/42; G01J 3/427
USPC .................................................. 356/369, 402
See application file for complete search history.

(56) References Cited

U.S. PATENT DOCUMENTS

| | | | | |
|---|---|---|---|---|
| 7,158,294 | B2 * | 1/2007 | Motomura | G02B 21/0084 250/459.1 |
| 2006/0151604 | A1 * | 7/2006 | Zhu | G06K 7/14 235/454 |
| 2007/0152556 | A1 | 7/2007 | Bohm | |
| 2010/0231722 | A1 | 9/2010 | Hill, Jr. et al. | |
| 2011/0164248 | A1 * | 7/2011 | Bushaw | G01J 3/427 356/318 |
| 2011/0218412 | A1 | 9/2011 | Tezuka et al. | |
| 2011/0221889 | A1 | 9/2011 | Knox et al. | |
| 2013/0292571 | A1 * | 11/2013 | Mukherjee | G01J 3/108 250/339.11 |

FOREIGN PATENT DOCUMENTS

| | | | |
|---|---|---|---|
| JP | 62-088932 | 4/1987 | |
| JP | 03-048138 | 3/1991 | |
| JP | 04-328449 | 11/1992 | |
| JP | 08-128916 | 5/1996 | |
| JP | 11-194089 | 7/1999 | |
| JP | 2000-009440 | 1/2000 | |
| JP | 2003-215032 | 7/2003 | |
| JP | 2007-010584 | 1/2007 | |
| JP | 2008-026036 | 2/2008 | |
| JP | 2008-275477 | 11/2008 | |
| JP | 2009-257919 | 11/2009 | |
| JP | 2009257919 | * 11/2009 | .............. G01J 3/427 |
| JP | 2010-025622 | 2/2010 | |
| JP | 2011-062301 | 3/2011 | |
| JP | 2011-131038 | 7/2011 | |
| JP | 2011-523065 | 8/2011 | |
| JP | 2012-154854 | 8/2012 | |
| WO | 2005/054924 | 6/2005 | |

OTHER PUBLICATIONS

International Search Report dated Sep. 16, 2014 in International (PCT) Application No. PCT/JP2014/003333.
Mutsuko Nakamura, Shigeki Nakauchi, "Moisturizing Effect of Skin Care Using NIR Imaging", Optics, 2010, vol. 39, No. 11, pp. 529-533 with partial English translation.
Machine translation of JP 2008-026036 submitted on Mar. 11, 2015.
Machine translation of JP 2011-062301 submitted on Mar. 11, 2015.
Machine translation of JP 08-128916 submitted on Mar. 11, 2015.
Machine translation of JP 2000-009440 submitted on Mar. 11, 2015.
Machine translation of JP 2003-215032 submitted on Mar. 11, 2015.

* cited by examiner

SPECTROSCOPIC APPARATUS

TECHNICAL FIELD

The present invention relates to a spectroscopic apparatus for acquiring absorption spectrum with a simple structure.

BACKGROUND ART

Some of conventional spectroscopic apparatuses use a lamp or a ceramic heater as a light source, and disperse light emitted from the light source and then transmitted through a material or reflected from a material, by a diffraction grating or by means of interference. In addition, some of spectroscopic apparatuses for detecting presence of a material scan a subject surface while sweeping the wavelength of laser light, thereby visualizing a 2-dimensional distribution of the material (see PATENT LITERATURE, NON PATENT LITERATURE, etc.).

CITATION LIST

Patent Literature

[PTL 1] Japanese Laid-Open Patent Publication No. 2012-154854
[PTL 2] Japanese Laid-Open Patent Publication No. 2010-025622

Non Patent Literature

[NPL 1] Mutsuko Nakamura, Shigeki Nakauchi, "Moisturizing effect of skin care using NIR imaging", Optics, 2010, vol. 39, no. 11, P. 529 to P. 533

SUMMARY OF THE INVENTION

However, in such conventional spectroscopic apparatuses as described above, a diffraction grating or an interference spectroscopic device is needed, thus causing a problem that the size of spectroscopic apparatuses is enlarged and the cost thereof increases.

The present invention is to solve the above conventional problem, and an object of the present invention is to provide a spectroscopic apparatus with small size and low cost.

To solve the above conventional problem, a spectroscopic apparatus according to one aspect of the present invention includes: a light radiating portion configured to radiate, to a target, light with a first wavelength which has a predetermined absorptivity for a specific object, and light with a second wavelength which has a smaller absorptivity for the specific object than the first wavelength; a light receiving portion configured to receive first scattered light obtained by light with the first wavelength transmitting through the target or being reflected by the target, and second scattered light obtained by light with the second wavelength transmitting through the target or being reflected by the target; and a measuring portion configured to generate information to be used for detection of the specific object at the target, based on a difference between the first scattered light and the second scattered light received by the light receiving portion.

It is noted that these overall or specific aspects may be realized by a system, a method, an integrated circuit, a computer program, or a computer-readable storage medium such as a CD-ROM, or may be realized by any combination of a system, a method, an integrated circuit, a computer program, or a storage medium.

The spectroscopic apparatus of the present invention can realize spectroscopic measurement with small size and low cost.

DESCRIPTION OF EMBODIMENTS

Figure 24:
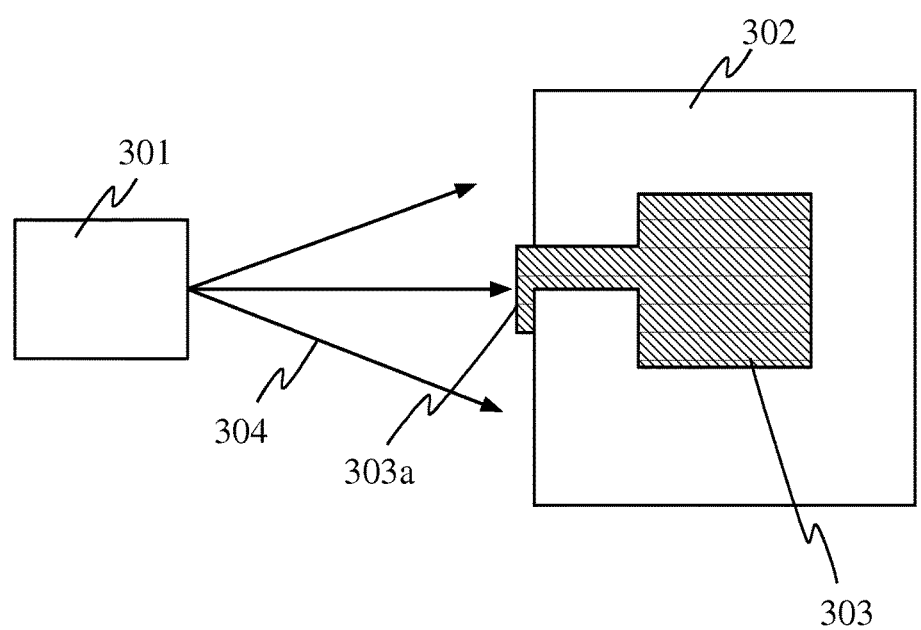
FIG. 24 is a diagram for explaining a conventional technique.

<Knowledge as Basis for the Present Invention>
FIG. 24 is a diagram for explaining a measurement method using a conventional liquid leakage detecting device 301 described in Patent Literature 1. In FIG. 24, the liquid leakage detecting device 301 radiates a middle infrared ray 304 with a wavelength of 2 μm to 25 μm to scan a surface of an oil sealing facility 302. The wavelength of the radiated middle infrared ray 304 is swept including 3.6 µm, which is an absorption wavelength of the oil 303. When a part of the oil 303 is leaked as a leaked oil 303a from the oil sealing facility 302, the radiated middle infrared ray 304 is absorbed by the leaked oil 303a, and the intensity of reflected scattered light reduces in the vicinity of 3.6 µm. Thus, the conventional liquid leakage detecting device 301 detects that the leaked oil 303a exists, by measuring the intensity of the reflected scattered light (calculating an absorption spectrum).

Patent Literature 2 and Non Patent Literature 1 disclose an examining device or method for a water amount distribution in a skin. These literatures describe a method in which light in a near-infrared wavelength region is radiated to a skin, the reflected light is taken with an infrared camera, and then operation processing is performed with use of a reflection intensity in a wavelength band in which light is easily absorbed by water and a reflection intensity in a wavelength band in which influence of absorption by water is small, thereby visualizing the water amount distribution.

However, the configurations of spectroscopic apparatuses described in the above conventional literatures require a diffraction grating or an interference spectroscopic device, resulting in a problem that the size of the spectroscopic apparatuses is enlarged and the cost thereof increases.

In addition, the conventional apparatus described in Patent Literature 1 needs to sweep the wavelength and therefore has a problem that it takes long time for measurement. In addition, although the reflected light is weak, the way to detect such weak light is not disclosed.

In addition, the conventional apparatuses described in Patent Literature 2 and Non Patent Literature 1 radiate near-infrared light to the entire surface of a skin at once. Therefore, a near-infrared light source is limited to one having a high intensity such as a halogen lamp, and an infrared camera which is expensive is used. Thus, there is a problem that the apparatuses are expensive.

<Method Focused on by the Present Inventors>

The present inventors focus on a specific wavelength at which a light absorptivity for an object that is a detection target becomes great, and set the wavelength of radiated light used in spectroscopic processing, based on the specific wavelength, thus newly devising a spectroscopic apparatus with small size and low cost.

Various aspects of the present invention based on the new devising are as follows.

<Summary of Aspects of Invention>

A spectroscopic apparatus according to one aspect of the present disclosure based on the present invention includes: a light radiating portion configured to radiate, to a target, light with a first wavelength which has a predetermined absorptivity for a specific object, and light with a second wavelength which has a smaller absorptivity for the specific object than the first wavelength; a light receiving portion configured to receive first scattered light obtained by light with the first wavelength transmitting through the target or being reflected by the target, and second scattered light obtained by light with the second wavelength transmitting through the target or being reflected by the target; and a measuring portion configured to generate information to be used for detection of the specific object at the target, based on a difference between the first scattered light and the second scattered light received by the light receiving portion.

For example, if the specific object is water, the first wavelength may be set to be equal to or longer than 1.4 µm and the second wavelength may be set to be equal to or shorter than 1.3 µm.

According to the above aspect, it becomes possible to generate information (for example, calculate an absorption spectrum) used for detection of a specific object, with use of an inexpensive solid-state light source, without using an expensive structure such as a diffraction grating. In addition, since it is not necessary to sweep a wavelength, measurement time can also be reduced. In addition, since, as well as an absorption wavelength (first wavelength), a wavelength (second wavelength) other than the absorption wavelength is used to compare detection results, detection of whether or not a specific object is present can be performed with high accuracy.

In the above aspect, the light radiating portion may include: a first solid-state light source configured to emit light with the first wavelength; a second solid-state light source configured to emit light with the second wavelength; and a light source control portion configured to drive the first and second solid-state light sources so that light with the first wavelength and light with the second wavelength are received in a discriminated manner by the light receiving portion. Thus, by using a solid-state light source, a spectroscopic apparatus can be realized with low cost.

Here, for example, the light source control portion may drive the first solid-state light source and the second solid-state light source with emission timings thereof shifted from each other, or may drive the first solid-state light source and the second solid-state light source so as to be modulated with different frequencies. Such configurations facilitate discrimination between light with the first wavelength and light with the second wavelength.

The light radiating portion may radiate light with the first wavelength and light with the second wavelength to the same position on the target, whereby the light receiving portion can receive reflected lights from the same position on the target. Thus, accuracy in detection of a specific object is improved.

The measuring portion may determine whether or not the specific object is present at the target, based on a ratio between an intensity of the first scattered light received by the light receiving portion and an intensity of the second scattered light received by the light receiving portion. For example, if the intensity of the second scattered light is greater than the intensity of the first scattered light, the measuring portion may determine that the specific object is present at the target.

Here, the first wavelength and the second wavelength may be set so that the ratio between the intensity of the first scattered light and the intensity of the second scattered light becomes equal to or greater than 10 when the specific object is present, whereby accuracy in determination is improved.

In addition, with regard to setting of the first wavelength and the second wavelength, the first wavelength and the second wavelength may be set so that a temperature-related change amount of absorptivity of light with the first wavelength for the specific object is ten times or more greater than a temperature-related change amount of absorptivity of light with the second wavelength for the specific object, whereby temperature change can be grasped from the ration between the intensity of the first scattered light and the intensity of the second scattered light.

In another aspect, the light radiating portion may include a scan processing portion configured to radiate light with the first wavelength and light with the second wavelength to the target so as to scan in a 2-dimensional direction. Further, an output portion may be provided which is configured to output whether or not the specific object is present at the target, as 2-dimensional area information, based on the scanning by the scan processing portion and the information generated by the measuring portion.

According to the above aspect, it becomes possible to detect whether or not a specific object is present at a target, as 2-dimensional area information.

Here, for example, the scan processing portion may first scan an entirety of the target in a spatially coarse manner, and if it is determined that the specific object is present, may next scan an area where the specific object is present, in a spatially dense manner, or the scan processing portion may first scan an entirety of the target in a temporally coarse manner, and if it is determined that the specific object is present, may next scan an area where the specific object is present, in a temporally dense manner. By scanning in this way, detection of an object at a target can be efficiently performed.

In another aspect, for example, a camera configured to take the target may be further provided, and the output portion may output 2-dimensional area information about whether or not the specific object is present at the target, with the 2-dimensional area information superimposed on a 2-dimensional image of the target taken by the camera.

According to the above aspect, it becomes possible to visually and easily grasp a location on a target where a specific object is present, by a 2-dimensional image.

In this case, the second wavelength may be set to an invisible wavelength in a range of wavelengths for which the camera has sensitivity, whereby a person present near the camera is prevented from being influenced.

In another aspect, for example, a distance measuring portion may be further provided which is configured to measure a distance to the target, and the output portion may add information about the distance measured by the distance measuring portion to 2-dimensional area information about whether or not the specific object is present at the target, and output a resultant information as 3-dimensional area information.

According to the above aspect, it becomes possible to easily grasp a location on a target where a specific object is present, by a 3-dimensional shape.

In another aspect, for example, a temperature measuring portion configured to measure a temperature of the target may be further provided, and the output portion may output 2-dimensional area information about whether or not the specific object is present at the target, with the 2-dimensional area information corrected in accordance with information about the temperature measured by the temperature measuring portion.

According to the above aspect, it becomes possible to appropriately correct determination for whether or not a specific object is present at a target, based on temperature.

It is noted that these overall or specific aspects may be realized by a system, a method, an integrated circuit, a computer program, or a computer-readable storage medium such as a CD-ROM, or may be realized by any combination of a system, a method, an integrated circuit, a computer program, or a storage medium.

Hereinafter, embodiments of the present invention will be specifically described with reference to the drawings.

Any of embodiments described below merely shows one specific example of the present invention. Numeric values, shapes, components, steps, the order of steps, etc. shown in the following embodiments are examples, and are not intended to limit the present invention. Among the components in the following embodiments, a component that is not recited in an independent claim indicating the most generic concept is described as an arbitrary component. Each content in all the embodiments may be combined with each other.

DETAILED DESCRIPTION OF EMBODIMENTS OF INVENTION

First Embodiment

Figure 1:
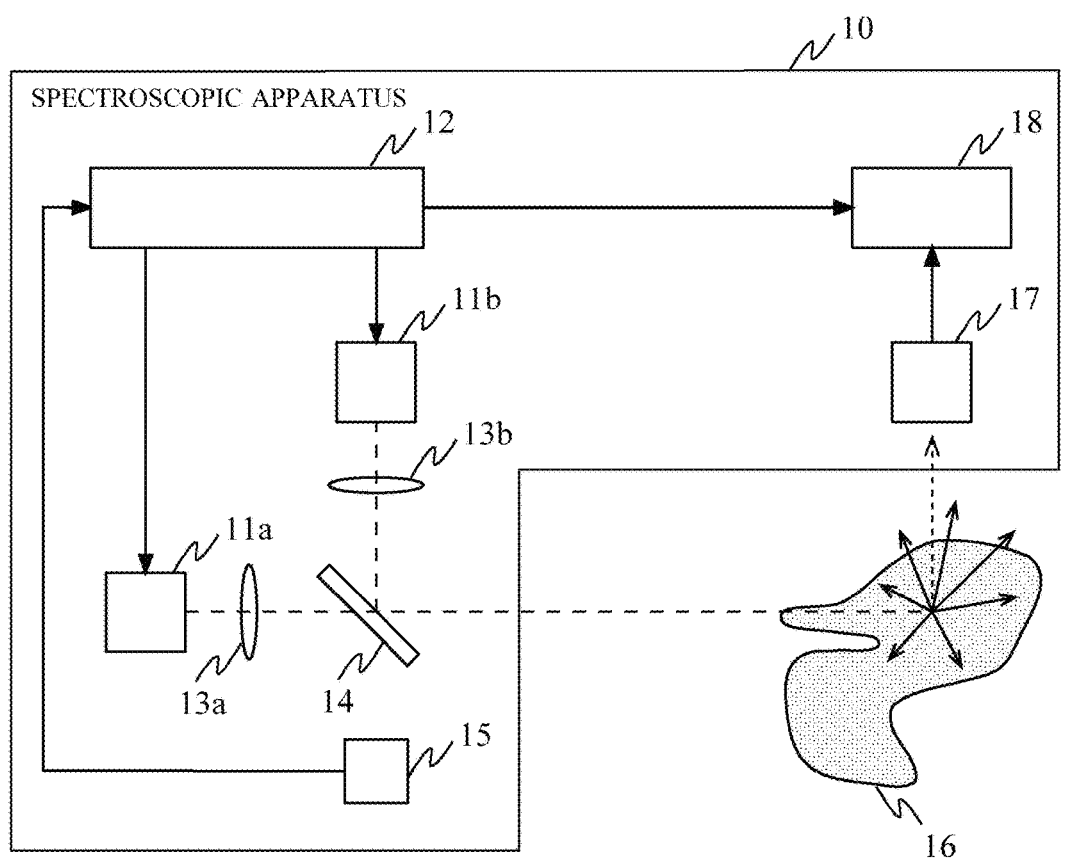
FIG. 1 is a configuration diagram of a spectroscopic apparatus 10 according to the first embodiment.

FIG. 1 is a configuration diagram of a spectroscopic apparatus 10 according to the first embodiment. The spectroscopic apparatus 10 radiates predetermined light to a subject body or a subject surface (hereinafter, referred to as a target) which is a part to be examined, and generates information that is useful for determining whether or not an object 16 to be detected is present at the target, based on scattered light (reflected light or transmitted light) from the target. The spectroscopic apparatus 10 shown in FIG. 1 includes solid-state light sources 11a and 11b, a light source control portion 12, lenses 13a and 13b, a wavelength-selective light branching element 14, a front light monitor 15, a light receiving portion 17, and a measuring portion 18.

First, each component of the spectroscopic apparatus 10 will be described.

The solid-state light source 11a is a light source that emits light with a wavelength of $\lambda 1$ as straight polarized light. The solid-state light source 11b is a light source that emits light with a wavelength of $\lambda 2$ as straight polarized light. The solid-state light sources 11a and 11b are placed such that a polarization plane of light emitted from the solid-state light source 11a and a polarization plane of light emitted from the solid-state light source 11b are collimated with each other. The wavelength $\lambda 1$ and the wavelength $\lambda 2$ are different. For example, a wavelength at which light is easily absorbed by the object 16 (absorptivity is great) is set as "$\lambda 1$", and a wavelength at which light is hardly absorbed by the object 16 relative to the wavelength $\lambda 1$ (absorptivity is small) is set as "$\lambda 2$". As the solid-state light sources 11a and 11b, a light emitting diode, a semiconductor laser, a super luminescent diode, etc. may be used. In the case of using a light emitting diode or a super luminescent diode, since the range of emitted light wavelengths is broad, the wavelength range may be narrowed by a filter.

In the present embodiment, the case where the number of solid-state light sources is two is described, but the number is not limited thereto. In the spectroscopic apparatus 10 of the present embodiment, at least two solid-state light sources may be provided, so three or more solid-state light sources may be provided. In this case, the wavelength-selective light branching element 14 and the lenses 13a and 13b described later may be added in the same manner.

The light source control portion 12 drives (controls) the solid-state light sources 11a and 11b so that the light receiving portion 17 can receive light with wavelength $\lambda 1$ and light with wavelength $\lambda 2$ in a discriminated manner. For example, the light source control portion 12 may alternately drive the solid-state light sources 11a and 11b so as to shift their phases from each other while performing modulation with the same frequency ((a) of FIG. 2), or may drive the solid-state light sources 11a and 11b with the same phase while performing modulation with different frequencies ((b) of FIG. 2). In the case of using different modulation frequencies as shown in (b) of FIG. 2, a separation degree of a lock-in amplifier can be enhanced as compared to the case of shifting phases while using the same modulation frequency as shown in (a) of FIG. 2, and therefore wavelength discrimination is facilitated. The light source control portion 12 may alternately drive the solid-state light sources 11a and 11b so as to shift their phases from each other while performing modulation with different frequencies, or may not necessarily perform modulation in the case of shifting phases. That is, as long as light with wavelength λ1 and light with wavelength λ2 can be received in a discriminated manner by the light receiving portion 17, the detailed driving method for the solid-state light sources 11a and 11b is not particularly limited.

The lens 13a receives light with wavelength λ1 emitted from the solid-state light source 11a and outputs the light as substantially collimated light to one surface of the wavelength-selective light branching element 14. The lens 13b receives light with wavelength λ2 emitted from the solid-state light source 11b and outputs the light as substantially collimated light to the other surface of the wavelength-selective light branching element 14.

The wavelength-selective light branching element 14 has a function of allowing transmission of light with wavelength λ1 and reflecting light with wavelength λ2. Therefore, the wavelength-selective light branching element 14 transmits the substantially collimated light with wavelength λ1 inputted to the one surface thereof from the lens 13a, and outputs the light from the other surface. Meanwhile, the wavelength-selective light branching element 14 reflects the substantially collimated light with wavelength λ2 inputted to the other surface from the lens 13b, and outputs the light from the other surface, with the angle of the light changed. As the wavelength-selective light branching element 14, a dichroic mirror, a dichroic prism, or the like may be used.

The solid-state light sources 11a and 11b, the lenses 13a and 13b, and the wavelength-selective light branching element 14 described above are placed such that a path of light with wavelength λ1 transmitted through the wavelength-selective light branching element 14 and a path of light with wavelength λ2 reflected by the wavelength-selective light branching element 14 substantially coincide with each other. The light with wavelength λ1 and the light with wavelength λ2 whose paths substantially coincide with each other become output light of the spectroscopic apparatus 10, which is radiated to a target.

The front light monitor 15 monitors the intensity of light with wavelength λ1 slightly reflected by the wavelength-selective light branching element 14 and the intensity of light with wavelength λ2 slightly transmitted through the wavelength-selective light branching element 14, and feeds back a result of the monitoring to the light source control portion 12. The light intensities that have been fed back are used for the light source control portion 12 to control outputs of the solid-state light sources 11a and 11b so as to be constant.

The light receiving portion 17 receives light scattered from a target when the light with wavelength λ1 and the light with wavelength λ2 (the output light of the spectroscopic apparatus 10) whose paths substantially coincide with each other are outputted from the wavelength-selective light branching element 14 and then radiated to the target. Then, the light receiving portion 17 outputs the received light to the measuring portion 18.

The measuring portion 18 sequentially receives the light received by the light receiving portion 17 and a drive signal which indicates a timing at which the light source control portion 12 drives the solid-state light sources 11a and 11b. Then, the measuring portion 18 calculates the intensity of light received by the light receiving portion 17 for the light with wavelength λ1 that has been radiated to and scattered by a target, and the intensity of light received by the light receiving portion 17 for the light with wavelength λ2 that has been radiated to and scattered by a target, and generates information that is useful for determining whether or not an object 16 is present at the target, based on those light intensities.

Next, with reference to FIG. 3, operation (spectroscopic processing) of the spectroscopic apparatus 10 in the first embodiment will be described.

Figure 2:
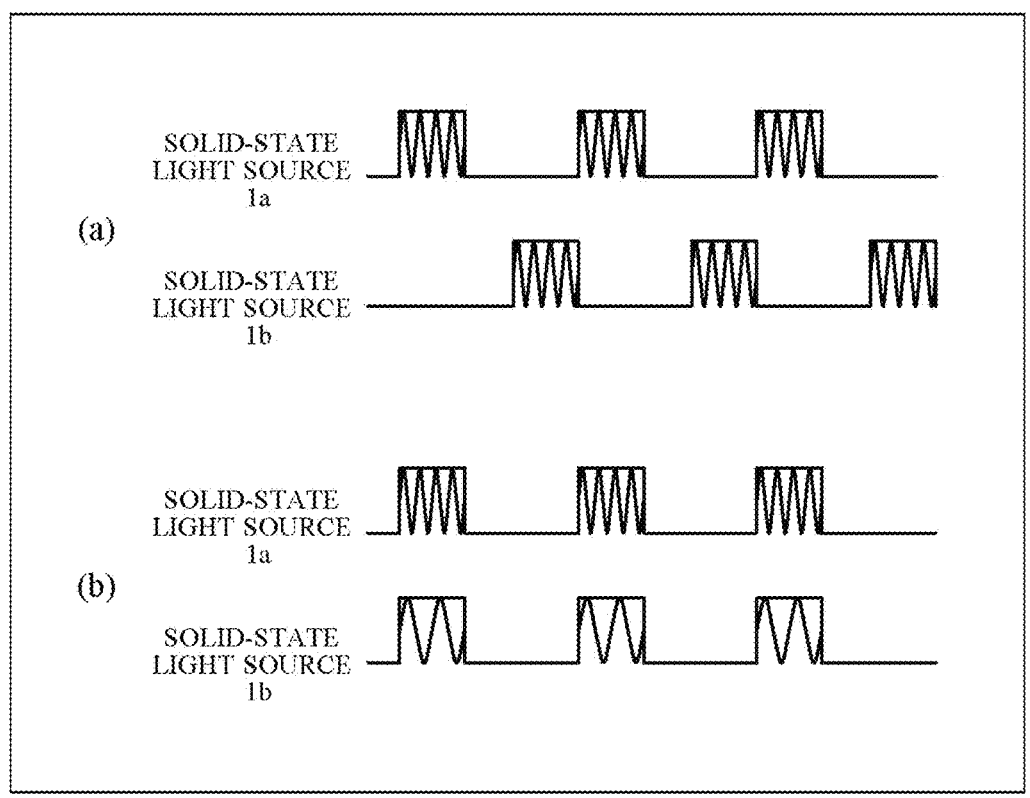
FIG. 2 is a diagram showing a driving method for the spectroscopic apparatus 10.
Figure 3:
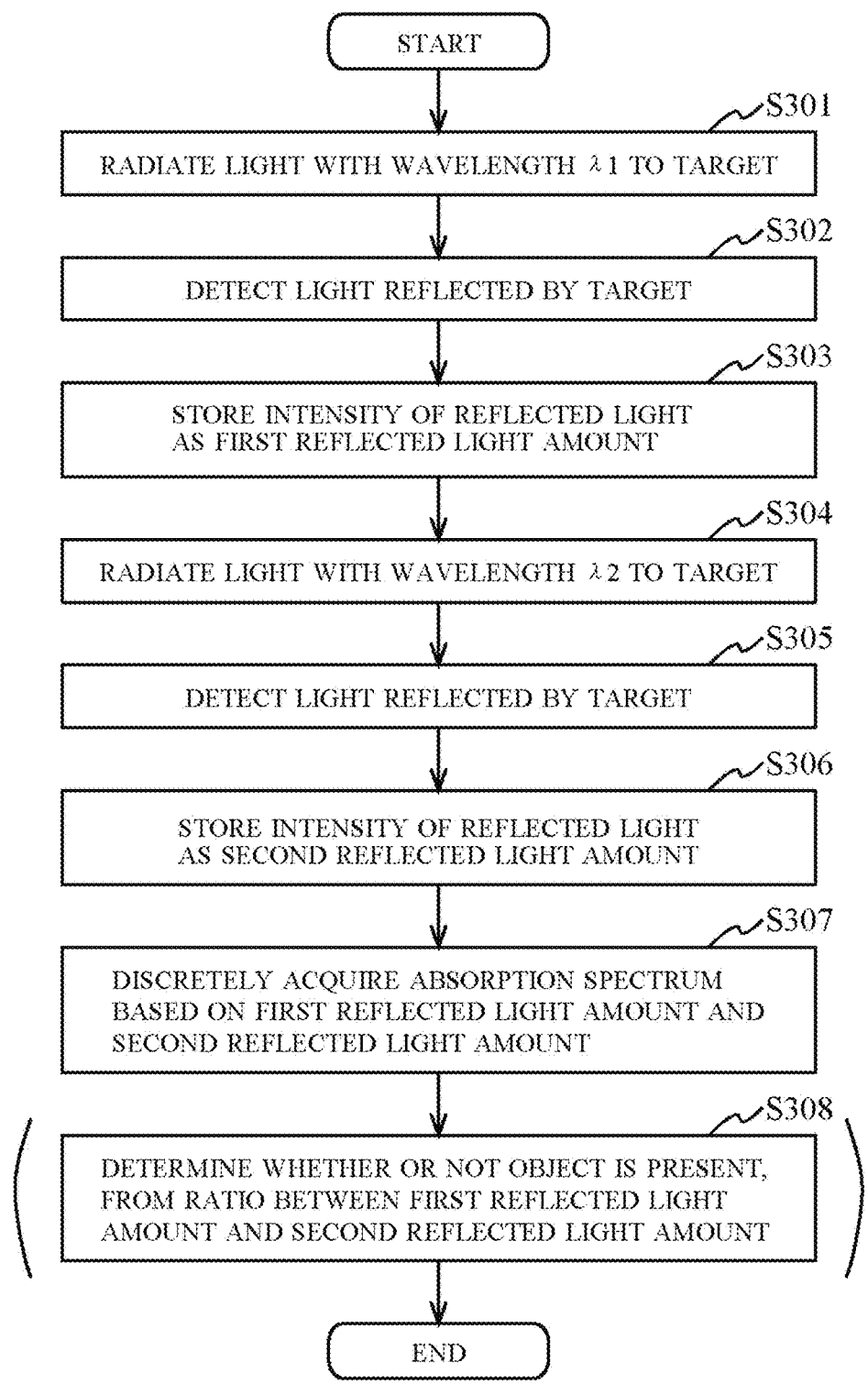
FIG. 3 is a flowchart for explaining operation of the spectroscopic apparatus 10.

In FIG. 3, operation of the spectroscopic apparatus 10 for measuring light reflected by a target when light is radiated thereto will be described based on, of the driving methods by the light source control portion 12 described above, the method of alternately driving the solid-state light source 11a and the solid-state light source 11b shown in (a) of FIG. 2.

First, the light source control portion 12 causes the solid-state light source 11a to emit light with wavelength λ1, which is radiated to the target (step S301). Along with this, the light receiving portion 17 detects light reflected by the target to which the light with wavelength λ1 has been radiated (step S302). The measuring portion 18 stores the intensity of the reflected light that has been detected, as a first reflected light amount (step S303). The light with wavelength λ1 from the solid-state light source 11a is emitted during a predetermined period.

Subsequently, the light source control portion 12 causes the solid-state light source 11b to emit light with wavelength λ2, which is radiated to the target (step S304). Along with this, the light receiving portion 17 detects light reflected by the target to which the light with wavelength λ2 has been radiated (step S305). The measuring portion 18 stores the intensity of the reflected light that has been detected, as a second reflected light amount (step S306). The light with wavelength λ2 from the solid-state light source 11b is emitted during a predetermined period.

Subsequently, the measuring portion 18 discretely calculates an absorption spectrum of the target based on the first reflected light amount and the second reflected light amount that have been stored and the drive signals for the solid-state light sources 11a and 11b acquired from the light source control portion 12 (step S307). Here, the measuring portion 18 can calculate the absorption spectrum based on the assumption that, if the reflected light amount obtained as a result of light radiation to the target is small, the wavelength of the radiated light is close to the wavelength of light that is absorbed by the target. That is, the absorption spectrum discretely calculated with respect to the light with wavelength λ1 and the light with wavelength λ2 is information that is useful for determining whether or not an object 16 to be detected is present at the target.

For the calculation of the absorption spectrum, as shown in FIG. 2, the light with wavelength λ1 and the light with wavelength λ2 may be each radiated to the target a plurality of times, to measure a plurality of light intensities, and the first reflected light amount and the second reflected light amount may be each obtained from the sum, average, distribution, etc. of the plurality of light intensities that have been measured, or a light intensity measured by one target irradiation may be used as the first reflected light amount and the second reflected light amount.

In the case where an absorption wavelength of an object 16 is known in advance and a wavelength at which light is easily absorbed is set as one of the wavelength λ1 or the wavelength λ2 and a wavelength at which light is hardly absorbed is set as the other one, the measuring portion 18 can further determine whether or not the object 16 is present at the target, from the absorption spectrum that has been discretely calculated (step S308).

For example, in the case where the intensity of light radiated to a target is denoted by I, a scattering reflection coefficient by the target is denoted by S, a light absorbance of the target is denoted by A, and the distance from the target to the light receiving portion 17 is denoted by L, an intensity (reflected light amount) D of reflected light detected by the light receiving portion 17 is represented by the following expression [1].

[Mathematical 1]

$$D \propto \frac{1}{L^2} SI10^{-A} \qquad [1]$$

Therefore, if an intensity $D_{\lambda 1}$ of reflected light with respect to the light with wavelength λ1 and an intensity $D_{\lambda 2}$ of reflected light with respect to the light with wavelength λ2 are obtained, and then a ratio ($=D_{\lambda 1}/D_{\lambda 2}$) of the two calculated intensities is calculated, it is possible to determine whether or not the object 16 is present at the target based on whether or not the ratio exceeds a predetermined threshold value. The threshold value can be freely set based on a light absorption characteristic of the object 16, the wavelength of radiated light, and the like. In addition, as the threshold value, an intensity ratio ($=D_{\lambda 1}/D_{\lambda 2}$) when it is known that the object 16 is not present at the target may be used.

As a specific example, the case where the object 16 is "water" will be described.

Figure 4:
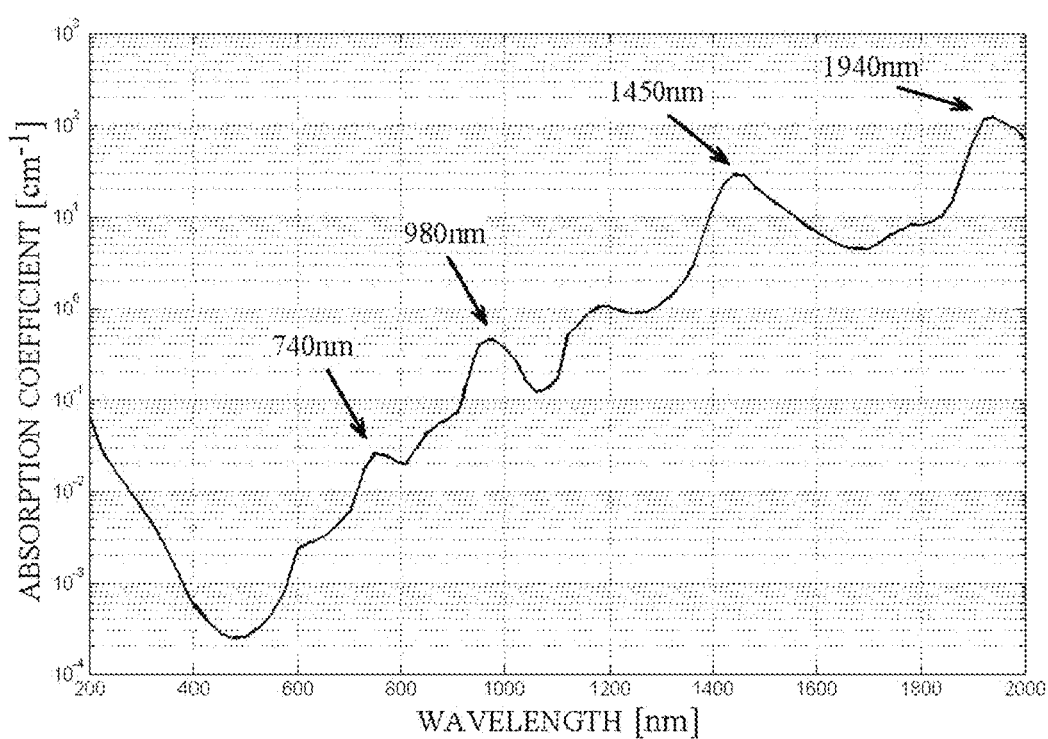
FIG. 4 is a diagram showing an absorption spectrum of water.

FIG. 4 is a diagram for explaining an absorption wavelength of water. As shown in FIG. 4, light absorption peaks of water appear at 1.94 μm, 1.45 μm, 0.98 μm, and 0.74 μm. Therefore, for example, light with a wavelength λ1 close to 1.45 μm is used for the solid-state light source 11a, and light with a wavelength λ2 not longer than 1.2 μm, at which the absorption coefficient is one digit or more smaller than for λ1, is used for the solid-state light source 11b.

Under the above condition, if there is no water at the target (for example, a subject surface such as a floor or a wall), the light with wavelength λ1 and the light with wavelength λ2 are both reflected and scattered while hardly being absorbed by the target, and therefore the ratio between the first reflected light amount and the second reflected light amount becomes "a value close to 1". On the other hand, if there is water at the target, the light with wavelength λ1 is greatly absorbed by water, but the light with wavelength λ2 is reflected and scattered without being much absorbed by water. Therefore, if the light radiation intensities are set such that a product between the intensity of the light with wavelength λ1 radiated to the target and a light reception sensitivity of the light receiving portion 17 for the light with wavelength λ1 is equal to a product between the intensity of the light with wavelength λ2 radiated to the target and a light reception sensitivity of the light receiving portion 17 for the light with wavelength λ2, the ratio of the first reflected light amount and the second reflected light amount becomes "a value equal to or greater than 10". Thus, it is possible to determine whether or not there is water from the ratio of the first reflected light amount and the second reflected light amount.

In the above embodiment, the case where whether or not an object 16 is present a target is determined based on scattered light reflected by the target has been described. However, since there is also a difference among lights transmitted through a target due to a difference in light absorption depending on the wavelength, it is also possible to determine whether or not an object 16 is present at a target based on scattered light transmitted through the target. In this case, the process can be achieved by replacing "reflection" with "transmission" in the flowchart shown in FIG. 3.

As described above, according to the spectroscopic apparatus 10 of the first embodiment, lights with different wavelengths are radiated from the two solid-state light sources 11a and 11b to a target, and light scattered from the target is received for each wavelength. Thus, an absorption spectrum of the target can be discretely obtained. The calculation of the absorption spectrum can be realized with low cost by the solid-state light sources alone without using an expensive device such as a diffraction grating, and in addition, it is not necessary to sweep the frequency, and therefore measurement time can also be reduced.

In addition, according to the spectroscopic apparatus 10, since, as well as light with a wavelength at which light is easily absorbed by an object 16 (absorption amount is large), light with a wavelength other than the absorption wavelength, at which light is hardly absorbed (absorption amount is small), is used, light amount change (variation) due to the shape, surface roughness, or dirt of a surface of the target can be corrected by a result of detection with respect to the wavelength at which light is hardly absorbed (absorption amount is small). Therefore, the present method using a plurality of wavelengths can detect more accurately whether or not an object 16 is present than in the case of using only a wavelength at which light is easily absorbed by an object 16.

In addition, according to the spectroscopic apparatus 10, since control is performed so as to alternately drive the solid-state light sources 11a and 11b, it is possible to obtain an absorption spectrum by using a single light receiving portion 17, thereby downsizing the apparatus. It is noted that in the case where the solid-state light sources 11a and 11b simultaneously radiate lights without modulation, two light receiving portions may be provided, one of which has a filter for passing light with wavelength λ1 and the other one of which has a filter for passing light with wavelength λ2.

In addition, according to the spectroscopic apparatus 10, since the solid-state light sources 11a and 11b are used, high-speed modulation can be performed, unlike the case of using a lamp light source or the like. In the case where the solid-state light sources 11a and 11b are driven so as to be modulated, by inputting modulation signals used for the driving as reference signals to the measuring portion 18, weak scattered light from a target can be amplified and measured by a known lock-in amplifier method, whereby signal-noise ratio can be increased. Thus, even under an environment having ambient light, stable measurement can be realized. The reference signals for the lock-in amplifier may be acquired from the front light monitor 15 and inputted to the measuring portion 18.

In addition, according to the spectroscopic apparatus 10, since paths of a plurality of lights emitted from the solid-state light sources 11a and 11b can be made to substantially coincide with each other (coaxial) by the wavelength-selective light branching element 14, lights with different wavelengths can be radiated to the same position on a target. Particularly, it is possible to make a plurality of lights emitted from a plurality of solid-state light sources substantially coincide with each other while scalably increasing the number of solid-state light sources. Thus, scalability for wavelength is ensured.

In the spectroscopic apparatus 10, the plurality of solid-state light sources 11a and 11b are separately provided from each other. However, the plurality of solid-state light sources 11a and 11b may be formed by being mounted on one semiconductor chip (by providing a plurality of emitters, for example), or may be formed by a wavelength-variable semiconductor laser whose wavelength can be changed by external control.

In the above configuration of the spectroscopic apparatus 10, if it is not necessary to control the intensity of light emitted from the solid-state light source 11a and the intensity of light emitted from the solid-state light source 11b so as to be constant, the front light monitor 15 may be omitted from among the above components of the spectroscopic apparatus 10. In addition, if lights emitted from the solid-state light sources 11a and 11b are already substantially collimated with each other, the lenses 13a and 13b may be omitted from among the above components of the spectroscopic apparatus 10. In addition, if paths of lights emitted from the solid-state light sources 11a and 11b are already the same, the wavelength-selective light branching element 14 may be omitted. Further, if the solid-state light sources 11a and 11b can radiate light with wavelength λ1 and light with wavelength λ2 so that the light receiving portion 17 can receive these lights in a discriminated manner, the light source control portion 12 may be omitted. In this sense, it can be said that the solid-state light sources 11a and 11b are the minimum configuration of "a light radiating portion" that is claimed.

Second Embodiment

Figure 5:
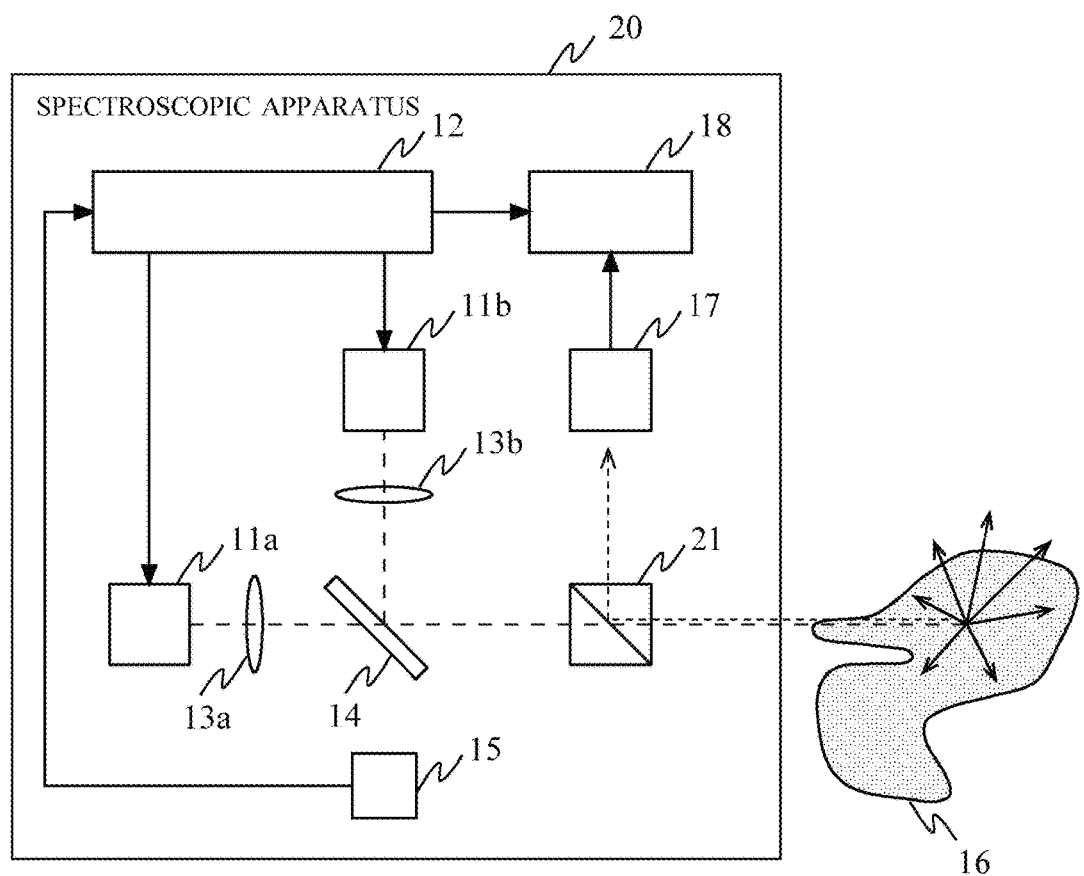
FIG. 5 is a configuration diagram of a spectroscopic apparatus 20 according to the second embodiment.

FIG. 5 is a configuration diagram of a spectroscopic apparatus 20 according to the second embodiment. The spectroscopic apparatus 20 includes the solid-state light sources 11a and 11b, the light source control portion 12, the lenses 13a and 13b, the wavelength-selective light branching element 14, the front light monitor 15, the light receiving portion 17, the measuring portion 18, and a polarization beam splitter 21.

The spectroscopic apparatus 20 is different from the above spectroscopic apparatus 10 in that the polarization beam splitter 21 is provided. Hereinafter, the different part will be described. The same components other than this are denoted by the same reference characters, and the description thereof is omitted.

The polarization beam splitter 21 is one component of "a light radiating portion" that is claimed, and is provided at an output destination of the wavelength-selective light branching element 14. The polarization beam splitter 21 is placed so as to transmit light inputted from the solid-state light sources 11a and 11b via the wavelength-selective light branching element 14 and output the transmitted light as P-polarization-component light to a target, and so as to reflect and output an S-polarization component of scattered light received from the target, to the light receiving portion 17.

Here, of the light radiated to the target, light that enters the inside of the target and is absorbed or reflected and scattered becomes random light including both P-polarization component and S-polarization component. On the other hand, light reflected on a surface of the target remains P-polarization-component light.

Therefore, of the light that is inputted to the polarization beam splitter 21 again after having been scattered from the target, an S-polarization component generated by light entering the inside of the target and being absorbed or reflected and scattered is reflected by the polarization beam splitter 21, and then received by the light receiving portion 17. On the other hand, P-polarization-component light reflected on a surface of the target is transmitted through the polarization beam splitter 21 without being reflected, and therefore is not received by the light receiving portion 17.

As described above, according to the spectroscopic apparatus 20 of the second embodiment, of light scattered from a target, only S-polarization-component light reflected by the polarization beam splitter 21 is received by the light receiving portion 17. Thus, a light component that is reflected on a surface without being absorbed by the target can be eliminated, whereby measurement with a high signal-noise ratio can be realized.

In addition, in the spectroscopic apparatus 20, since light reflected from a target (scattered reflected light), instead of light transmitted through a target, is inputted to the polarization beam splitter 21, the light receiving portion 17 can be placed at the same side as the solid-state light sources 11a and 11b, whereby the size of the apparatus can be reduced.

Third Embodiment

Figure 6:
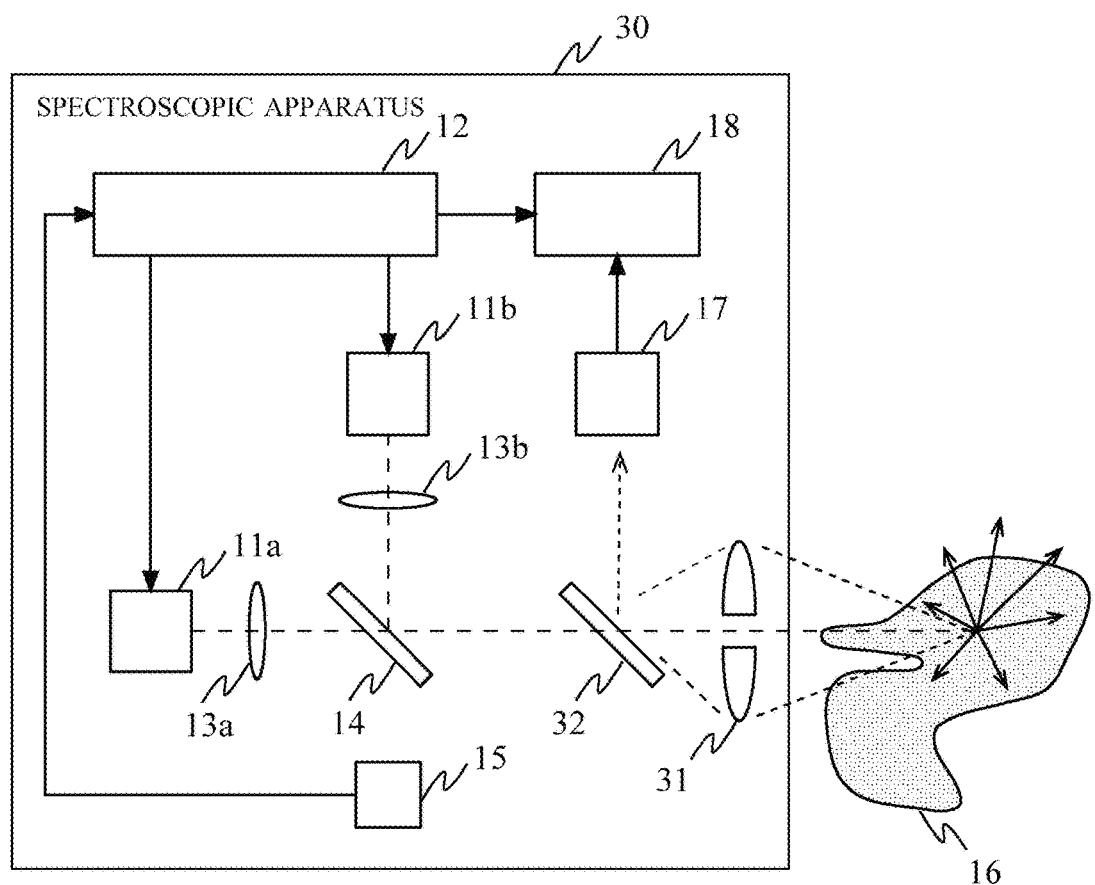
FIG. 6 is a configuration diagram of a spectroscopic apparatus 30 according to the third embodiment.

FIG. 6 is a configuration diagram of a spectroscopic apparatus 30 according to the third embodiment. The spectroscopic apparatus 30 includes the solid-state light sources 11a and 11b, the light source control portion 12, the lenses 13a and 13b, the wavelength-selective light branching element 14, the front light monitor 15, the light receiving portion 17, the measuring portion 18, a holed lens 31, and a half mirror 32.

The spectroscopic apparatus 30 is different from the above spectroscopic apparatus 10 in that the holed lens 31 and the half mirror 32 are provided. Hereinafter, the different part will be described. The same components other than this are denoted by the same reference characters, and the description thereof is omitted.

The half mirror 32 and the holed lens 31 are each one component of "a light radiating portion" that is claimed, and are provided in this order at the output destination of the wavelength-selective light branching element 14. The half mirror 32 is placed so as to transmit lights inputted from the solid-state light sources 11a and 11b via the wavelength-selective light branching element 14, and input the lights to the holed lens 31, and so as to output light inputted from the holed lens 31, to the light receiving portion 17. The holed lens 31 is a condensing lens that is holed, and is placed so that light transmitted through the half mirror 32 passes through the hole and is outputted to a target, and scattered light inputted from the target is collected by the lens and returned to the half mirror 32.

Lights emitted from the solid-state light sources 11a and 11b pass through a hole portion of the holed lens 31 via the wavelength-selective light branching element 14 and the half mirror 32, and is radiated to a target. Scattered light reflected from the target is collected over a wide range by the holed lens 31, and then a part of the collected light is outputted to the light receiving portion 17 by the half mirror 32.

As described above, according to the spectroscopic apparatus 30 of the third embodiment, light scattered from a target can be received over a wide range by using the holed lens 31, whereby the light reception amount is increased. Therefore, it becomes possible to accurately perform calculation of a discrete absorption spectrum of a target and detection for whether or not an object 16 is present.

Instead of the half mirror 32, the polarization beam splitter 21 described in the second embodiment may be used.

Fourth Embodiment

Figure 7:
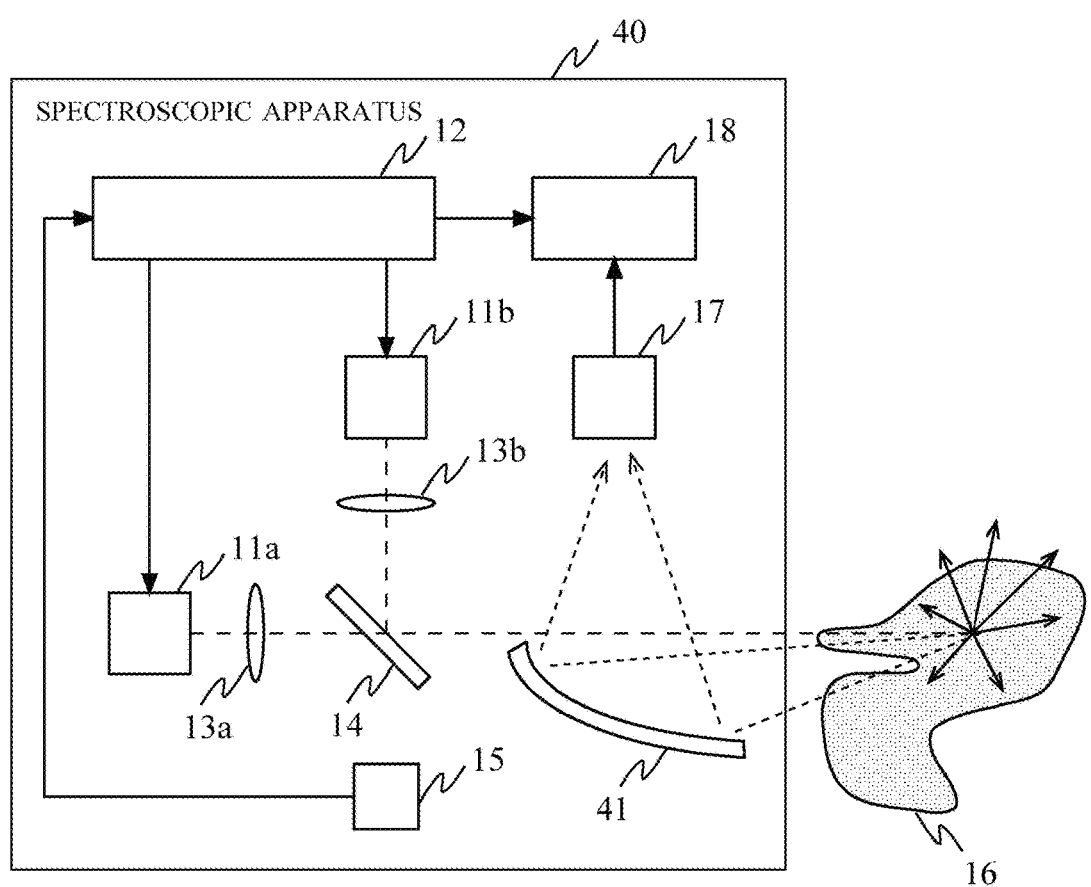
FIG. 7 is a configuration diagram of a spectroscopic apparatus 40 according to the fourth embodiment.

FIG. 7 is a configuration diagram of a spectroscopic apparatus 40 according to the fourth embodiment. The spectroscopic apparatus 40 includes the solid-state light sources 11a and 11b, the light source control portion 12, the lenses 13a and 13b, the wavelength-selective light branching element 14, the front light monitor 15, the light receiving portion 17, the measuring portion 18, and a parabolic mirror 41.

The spectroscopic apparatus 40 is different from the above spectroscopic apparatus 10 in that the parabolic mirror 41 is provided. Hereinafter, the different part will be described. The same components other than this are denoted by the same reference characters, and the description thereof is omitted.

The parabolic mirror 41 is one component of "a light radiating portion" that is claimed, and is a concave mirror whose reflection surface is a rotational parabolic surface formed by rotating a parabola with respect to its axis. The parabolic mirror 41 is placed so that scattered light reflected from a target is collected over a wide range and a focal point of light is formed on the light receiving portion 17. The parabolic mirror 41 shown in FIG. 7 is an off-axis parabolic mirror.

As described above, according to the spectroscopic apparatus 40 of the fourth embodiment, light scattered from a target can be received over a wide range by using the parabolic mirror 41, whereby the light reception amount is increased. Therefore, it becomes possible to accurately perform calculation of a discrete absorption spectrum of a target and detection for whether or not an object 16 is present. In addition, since the parabolic mirror 41 is a reflection-type optical device, it is not necessary to take into consideration influence of chromatic aberration due to wavelength difference among the solid-state light sources, as compared to the case of using a lens.

Fifth Embodiment

In the above first to fourth embodiments, spectroscopic apparatuses that perform calculation of a discrete absorption spectrum and detection for whether or not an object 16 is present, at one point of a target, have been described.

In the fifth and subsequent embodiments, spectroscopic apparatuses that perform calculation of a discrete absorption spectrum and detection for whether or not an object 16 is present, 2-dimensionally and over a wide area of a target, will be described.

Figure 8:
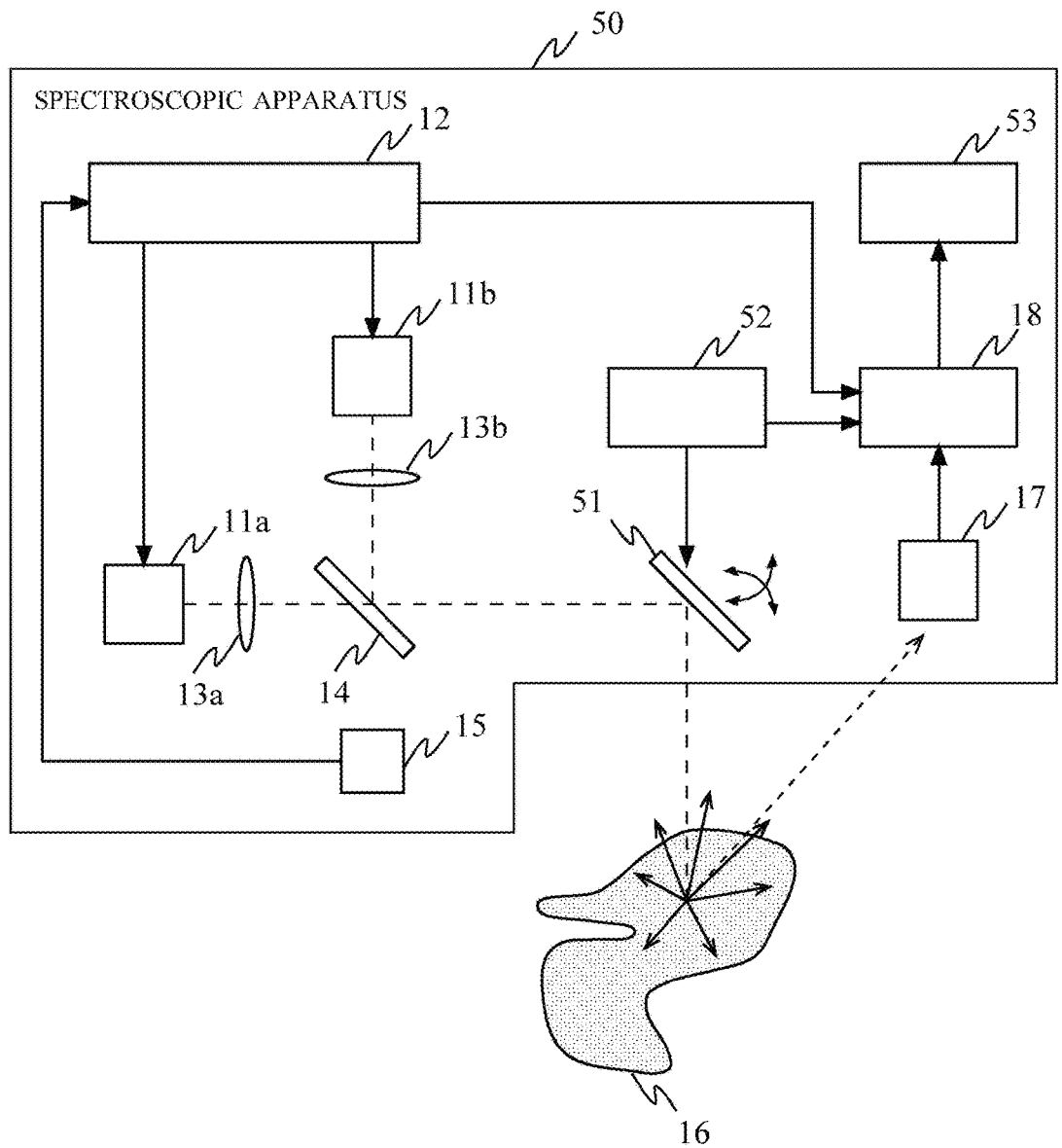
FIG. 8 is a configuration diagram of a spectroscopic apparatus 50 according to the fifth embodiment.

FIG. 8 is a configuration diagram of a spectroscopic apparatus 50 according to the fifth embodiment. The spectroscopic apparatus 50 includes the solid-state light sources 11a and 11b, the light source control portion 12, the lenses 13a and 13b, the wavelength-selective light branching element 14, the front light monitor 15, the light receiving portion 17, the measuring portion 18, a scanning portion 51, a scan driving portion 52, and an output portion 53.

The spectroscopic apparatus 50 is different from the above spectroscopic apparatus 10 in that the scanning portion 51, the scan driving portion 52, and the output portion 53 are provided. These different components are part of "a light radiating portion" that is claimed. Hereinafter, the different part will be described. The same components other than this are denoted by the same reference characters, and the description thereof is omitted.

The scanning portion 51 is an optical component that receives light emitted from the solid-state light sources 11a and 11b, and reflects the light to be radiated to a target while scanning in 2-dimensional directions. The scanning portion 51 is placed on a path of light with wavelength λ1 and light with wavelength λ2. As the scanning portion 51, a known device may be used such as a galvano mirror, a polygon mirror, a MEMS mirror of electromagnetically-driven type or electrostatically-driven type, or an acoustic optical deflector.

The scan driving portion 52 controls a scanning angle of the scanning portion 51 so that light radiated to a target scans in 2-dimensional directions, and outputs the scanning angle to the measuring portion 18. When having acquired the scanning angle from the scan driving portion 52, the measuring portion 18 stores the scanning angle (scan point) of the scanning portion 51 and the intensity (reflected light amount) of reflected light detected by the light receiving portion 17, so as to be 2-dimensionally associated with each other based on a desired resolution, a sampling rate, or the like. The 2-dimensional information stored in the measuring portion 18 is outputted to the output portion 53. The scanning portion 51 and the scan driving portion 52 compose "a scan processing portion" that is claimed.

The output portion 53 is an interface (for example, a display, a printer, a speaker, etc.) that presents the 2-dimensional information given from the measuring portion 18 by an image, a sound, or the like. If it is not necessary to present the 2-dimensional information given from the measuring portion 18 visually or aurally to a user or the like of the spectroscopic apparatus 50, the output portion 53 may be omitted.

Hereinafter, with reference to FIG. 9, operation (spectroscopic processing) of the spectroscopic apparatus 50 according to the fifth embodiment will be described.

Figure 9:
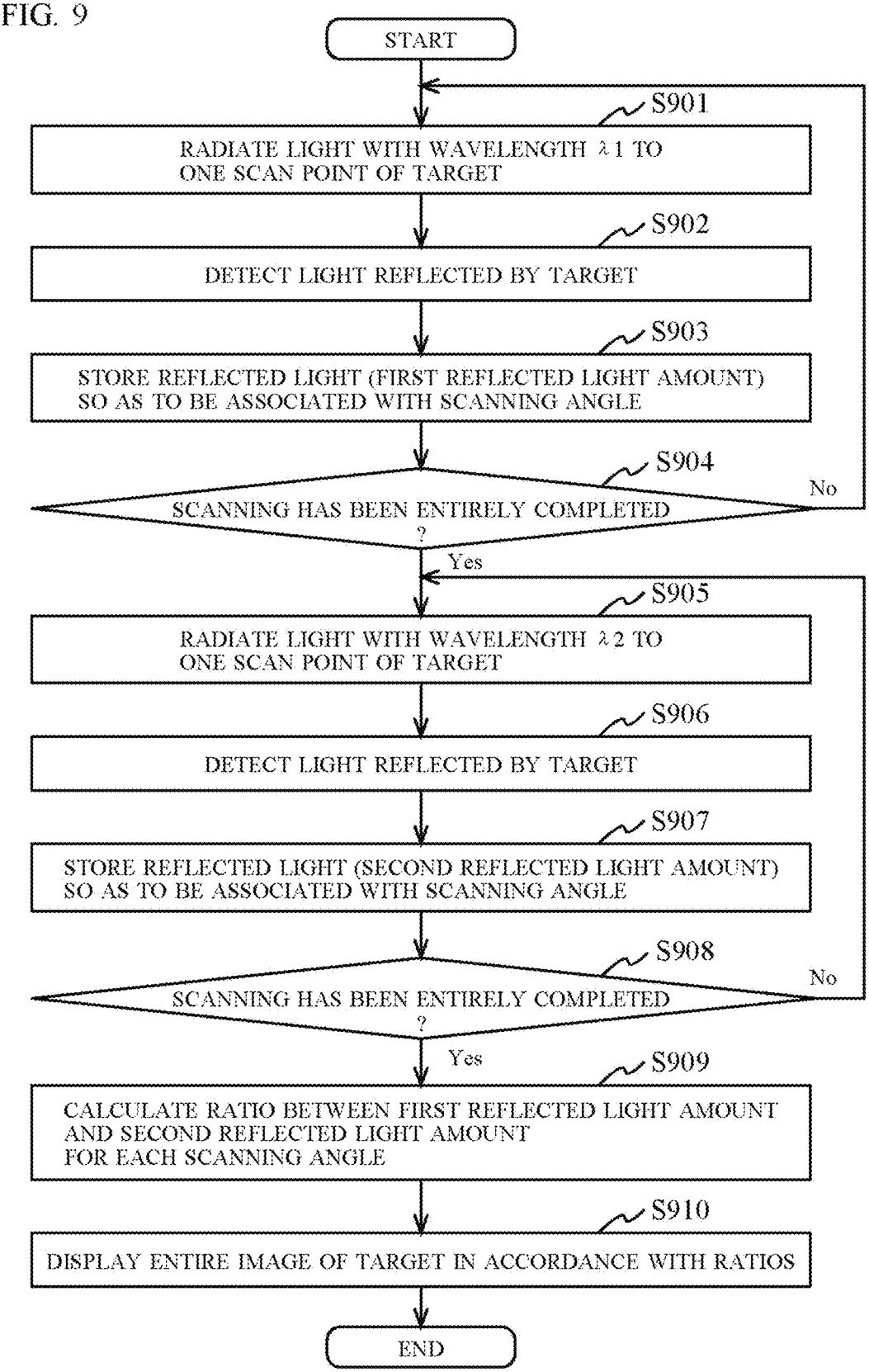
FIG. 9 is a flowchart for explaining operation of the spectroscopic apparatus 50.

FIG. 9 is a diagram showing an operation flowchart of the spectroscopic apparatus 50 which includes the scanning portion 51, scan driving portion 52, and the output portion 53. Also in FIG. 9, as in the above FIG. 3, operation of the spectroscopic apparatus 50 for measuring light reflected by a target when light is radiated thereto will be described based on the method of alternately driving the solid-state light source 11a and the solid-state light source 11b.

First, the light source control portion 12 causes the solid-state light source 11a to emit light with wavelength λ1, which is inputted to the scanning portion 51 via the lens 13a and the wavelength-selective light branching element 14, and then the light is radiated from the scanning portion 51 to a target. Here, the scan driving portion 52 controls the scanning angle of the scanning portion 51 so as to radiate the light with wavelength λ1 to one scan point of the target (step S901). In response, the light receiving portion 17 detects light reflected from the one scan point of the target to which the light with wavelength λ1 has been radiated (step S902). The measuring portion 18 stores the intensity (first reflected light amount) of the reflected light detected by the light receiving portion 17, so as to be associated with the scanning angle of the scanning portion 51 (step S903). The processing of steps S901 to S903 is repeatedly performed until scanning for the entire target (all scan points) is completed (step S904).

After the scanning by the light with wavelength λ1 is completed, next, the light source control portion 12 causes the solid-state light source 11b to emit light with wavelength λ2, which is inputted to the scanning portion 51 via the lens 13b and the wavelength-selective light branching element 14, and then the light is radiated from the scanning portion 51 to the target. As in the above, the scan driving portion 52 controls the scanning angle of the scanning portion 51 so as to radiate the light with wavelength λ2 to one scan point of the target (step S905). In response, the light receiving portion 17 detects light reflected from the one scan point of the target to which the light with wavelength λ2 has been radiated (step S906). The measuring portion 18 stores the intensity (second reflected light amount) of the reflected light detected by the light receiving portion 17, so as to be associated with the scanning angle of the scanning portion 51 (step S907). The processing of steps S905 to S907 is repeatedly performed until scanning for the entire target (all scan points) is completed (step S908). Here, procedures of scanning by lights with wavelengths λ1 and λ2 are not particularly limited.

After the scanning by the light with wavelength λ2 is completed, the ratio of the first reflected light amount and the second reflected light amount is calculated for each scanning angle (step S909). Then, the ratio calculated for each scanning angle is processed to be, for example, 2-dimensional image data whose display manner differs in accordance with the magnitude of the ratio, and the data is given to the output portion 53 so as to be displayed on a screen (step S910).

As described above, according to the spectroscopic apparatus 50 of the fifth embodiment, lights with different wavelengths from the solid-state light sources 11a and 11b are radiated so as to scan on a target by using the scanning portion 51, and scattered light from the target is received for each wavelength by the light receiving portion 17. Therefore, based on comparison of the amounts of lights received by the measuring portion 18, a spatial distribution of the target can be imaged. That is, a position where an object 16 is present on the target can be detected.

A scan interval of the scanning portion 51 can be freely set. For example, first, the entire target may be coarsely scanned with a broad scan interval or a long time interval, and next, an area where it is found an object 16 is present may be scanned in detail (densely) with a narrow scan interval or a short time interval. Alternatively, for example, first, scan for the entire target may be started with a broad scan interval or a long time interval, and then, from a point when presence of an object 16 is found, may be switched to scan with a narrow scan interval or a short time interval. Thus, a position where an object 16 is present in the entire target can be efficiently detected. In this way, by switching the scanning between coarse and dense in a spatial manner or a temporal manner individually or by combination in accordance with whether or not an object 16 is present, when the object 16 is not present, the scanning cycle becomes fast and power consumption of the light sources can be reduced, and when the object 16 is present, the object 16 can be measured in detail, thus enabling adaptive measurement.

Although it is preferable that the scanning portion 51 performs 2-dimensional scanning, the scanning portion 51 may perform 1-dimensional scanning. In the case where the scanning portion 51 performs only 1-dimensional scanning, if a target or the spectroscopic apparatus 50 is moved in a direction perpendicular to the 1-dimensional scanning direction, a 2-dimensional distribution can be consequently acquired.

In the spectroscopic apparatuses 10 to 40 of the above first to fourth embodiments which do not include the scanning portion 51 and the scan driving portion 52 for 2-dimensionally radiating light to a target, it is necessary to place the solid-state light sources 11a and 11b, the lenses 13a and 13b, and the wavelength-selective light branching element 14 such that a path of light with wavelength λ1 transmitted through the wavelength-selective light branching element 14 and a path of light with wavelength λ2 reflected by the wavelength-selective light branching element 14 substantially coincide with each other.

However, if positional displacement (amount or direction) between two light paths is known in advance, the positional displacement can be corrected by scan control or by performing calculation with the acquired data shifted by a time (timing) corresponding to the positional displacement, whereby the two light paths can be made to substantially coincide with each other on the target. Therefore, in spectroscopic apparatuses that include the scanning portion 51 and the scan driving portion 52 in the subsequent embodiments, the two light paths may be displaced from each other within a range in which the positional displacement can be absorbed by such scan control or calculation.

Figure 10:
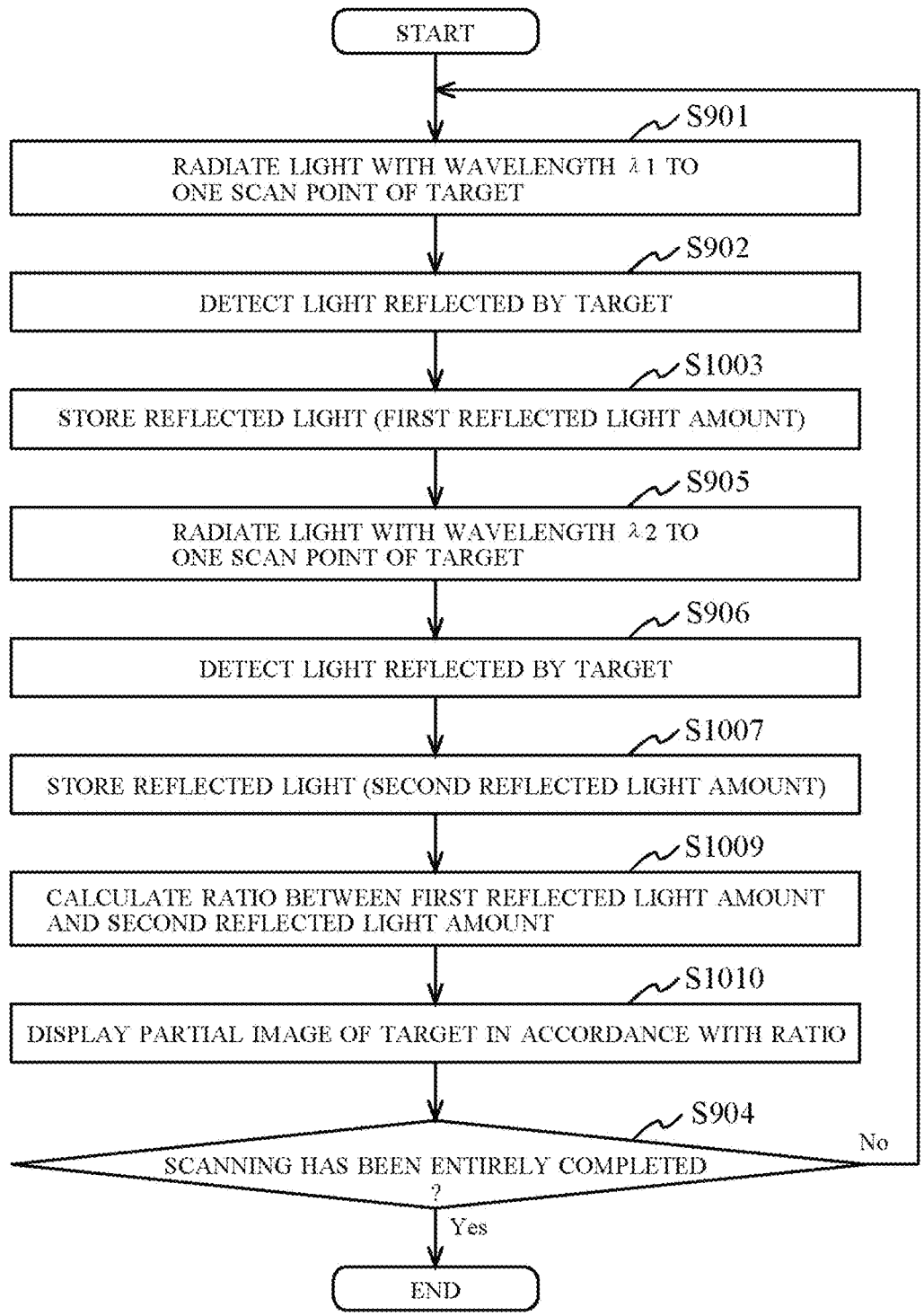
FIG. 10 is a flowchart for explaining another operation of the spectroscopic apparatus 50.

In the process in the operation flowchart shown in FIG. 9, the case where, first, scanning by light with wavelength λ1 is completely performed, next, scanning by light with wavelength λ2 is completely performed, and thereafter, an image of the entire target is displayed, has been shown. However, instead of this method, as shown in FIG. 10, radiation, measurement, and storing for light with wavelength λ1 (step S901, S902, S1003) and radiation, measurement, and storing for light with wavelength λ2 (step S905, S906, S1007) may be sequentially performed per one scan point of a target, and every time the ratio of light amounts is obtained at one scan point (step S1009), a partial image of the target may be displayed (step S1010). The unit of processing may be a plurality of scan points (one scan line).

Thus, if the unit of processing is made small, the amount of image data temporarily stored for image display (ratio calculation) is only an amount corresponding to one or a plurality of scan points. Therefore, an effect of reducing a necessary memory amount is obtained.

In the process of the operation flowchart shown in FIG. 9, if the wavelength λ1 and the wavelength λ2 are set to a wavelength at which a light absorption amount by an object 16 is large and a wavelength at which a light absorption amount by the object 16 is small, presence and absence of the object 16 can be imaged from the ratio of the first reflected light amount and the second reflected light amount. However, there is a possibility that another material having a characteristic close to that of the object 16 with respect to lights with wavelength λ1 and wavelength λ2 might be erroneously detected. In addition, there is also an area (non processing target area) that should be excluded from a range for which spectroscopic processing is performed. Accordingly, a process of an operation flowchart shown in FIG. 11 may be performed.

Figure 11:
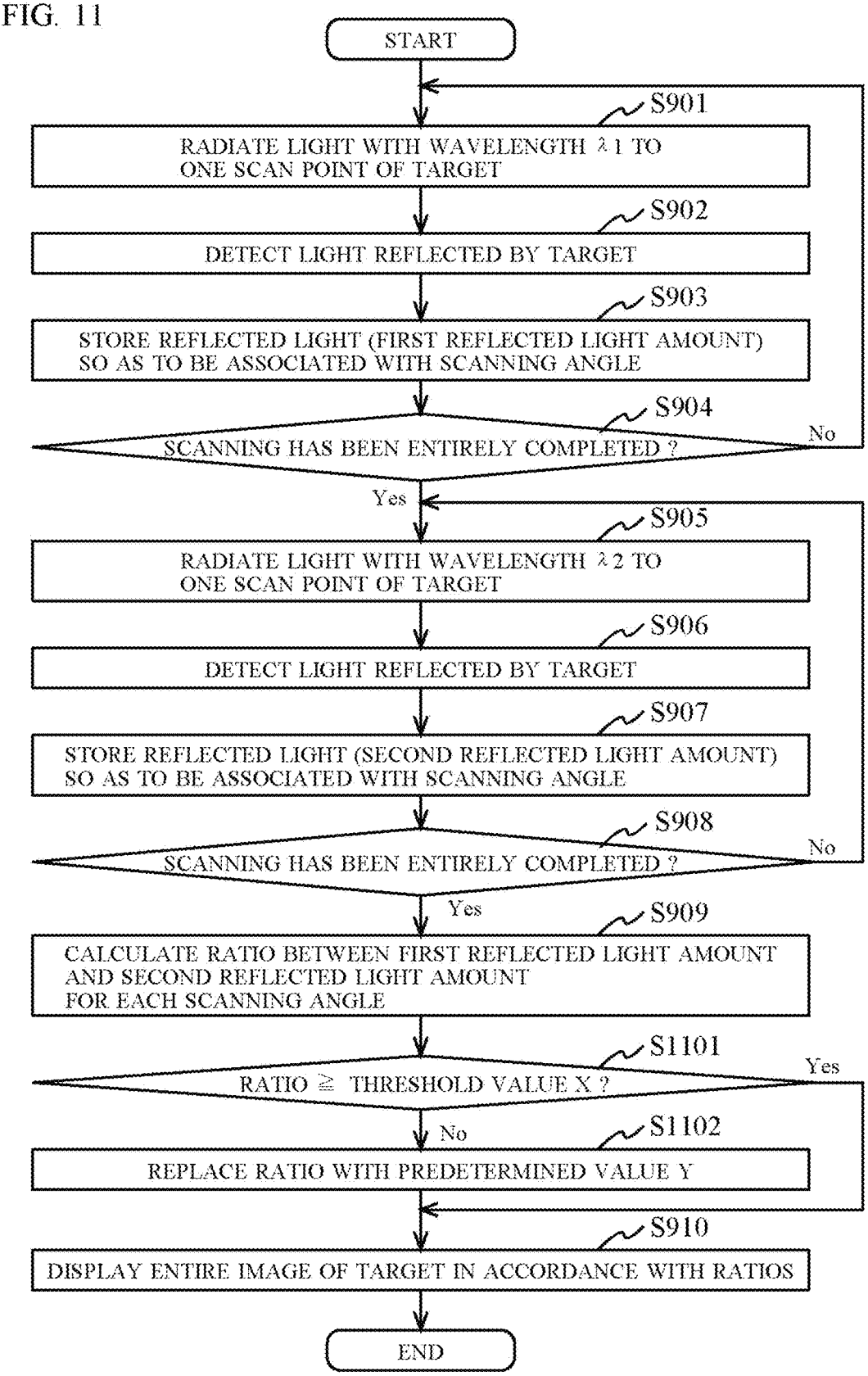
FIG. 11 is a flowchart for explaining still another operation of the spectroscopic apparatus 50.

In the process of the operation flowchart shown in FIG. 11, after the ratio of the first reflected light amount and the second reflected light amount is calculated (step S909), the calculated ratio is compared with a predetermined threshold value X (step S1101). As a result of the comparison, if the ratio is equal to or greater than the threshold value X, the ratio is directly displayed as an image on the output portion 53, and if the ratio is smaller than the threshold value X, the ratio is replaced with a predetermined value Y and the predetermined value Y is displayed as an image on the output portion 53 (step S1102). An area in a target for which the ratio is replaced with the predetermined value Y may be stored in the measuring portion 18, the output portion 53, or the like.

Here, if the threshold value X is set between a ratio based on the object 16 and a ratio based on another material having a characteristic close to the object 16, or if the threshold value X is set between a ratio based on the object 16 and a ratio based on a non processing target area, the other material or the non processing target area that has been erroneously detected can be displayed as an image in a display manner that is based on the predetermined value Y. The threshold value X may be set in advance before execution of the spectroscopic processing, or may be set by confirming an initial image displayed after the spectroscopic processing has been executed. The ratio for the non processing target area may be acquired by performing in advance spectroscopic processing for a target when the object 16 is not present. The predetermined value Y may be a value out of a range of values that can be taken by the ratio of the first reflected light amount and the second reflected light amount on the object 16. For example, the maximum value or the minimum value that can be displayed on the output portion 53 may be selected as the predetermined value Y.

Thus, another material having a characteristic close to that of an object 16 or a non processing target area can be displayed as an image always by the predetermined value Y, whereby erroneous display of another material or erroneous display in the non processing target area is decreased.

Instead of the method of comparing the ratio of the first reflected light amount and the second reflected light amount with the threshold value X, a method of comparing the first reflected light amount with respect to the wavelength $\lambda 1$ at which light is easily absorbed by an object 16, with the threshold value X, may be used. In this case, the threshold value X may be set between the first reflected light amount based on an object 16 and the first reflected light amount based on another material having a characteristic close to the object 16, or may be set between the first reflected light amount based on the object 16 and the first reflected light amount based on a non processing target area.

The step of comparing the ratio with the threshold value X (step S1101) and the step of replacing only the ratio that is smaller than the threshold value X with the predetermined value Y (step S1102) shown in FIG. 11 can be applied also to the operation flowchart shown in FIG. 10 in the same manner.

Sixth Embodiment

Figure 12:
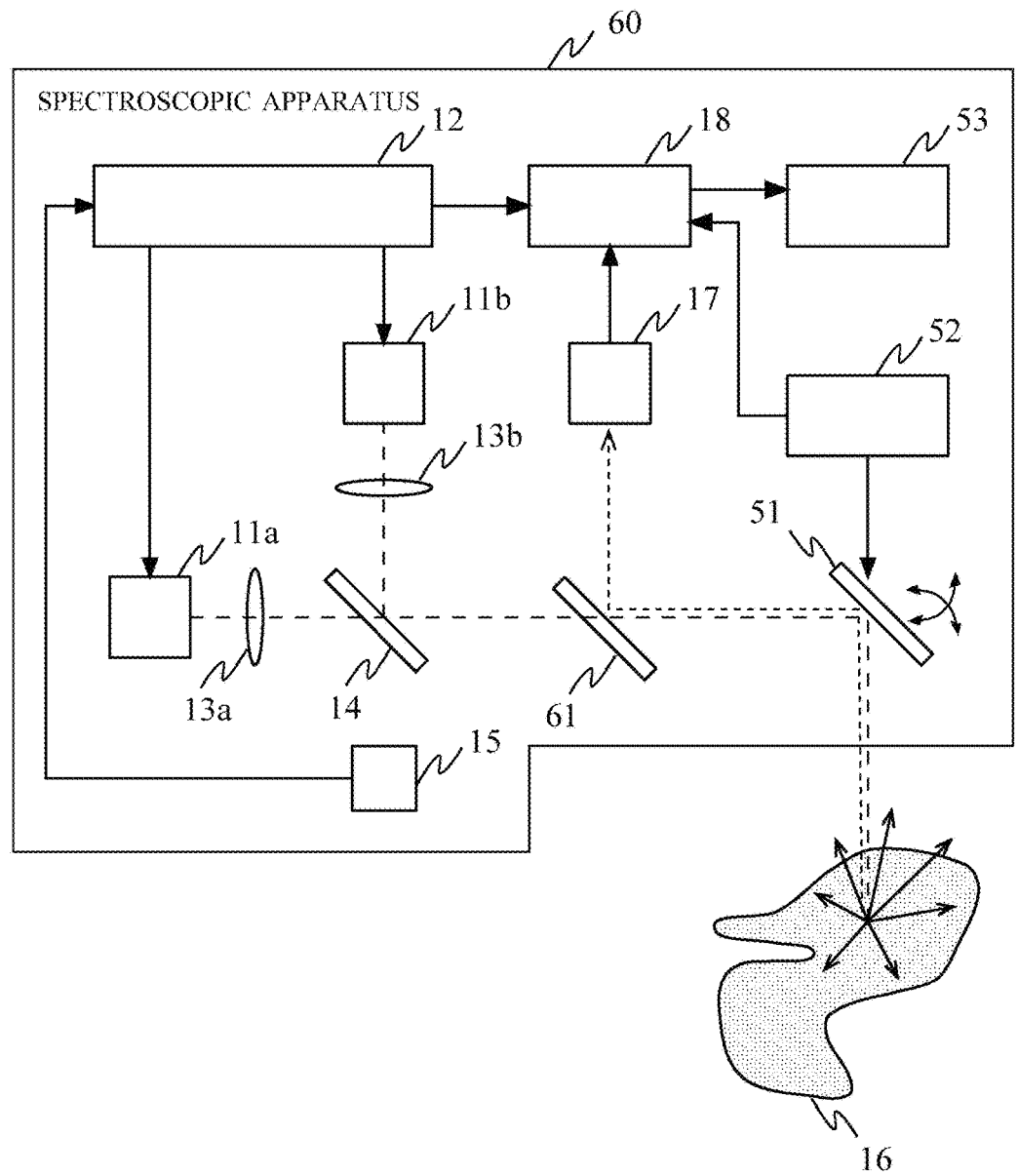
FIG. 12 is a configuration diagram of a spectroscopic apparatus 60 according to the sixth embodiment.

FIG. 12 is a configuration diagram of a spectroscopic apparatus 60 according to the sixth embodiment. The spectroscopic apparatus 60 includes the solid-state light sources 11a and 11b, the light source control portion 12, the lenses 13a and 13b, the wavelength-selective light branching element 14, the front light monitor 15, the light receiving portion 17, the measuring portion 18, the scanning portion 51, the scan driving portion 52, the output portion 53, and a half mirror 61.

The spectroscopic apparatus 60 is different from the spectroscopic apparatus 50 in that the half mirror 61 is provided and the light receiving portion 17 is located at the same side as the solid-state light sources 11a and 11b. Hereinafter, the different part will be described. The same components other than this are denoted by the same reference characters, and the description thereof is omitted.

The half mirror 61 is placed so as to transmit light inputted from the solid-state light sources 11a and 11b via the wavelength-selective light branching element 14 and output the light to the scanning portion 51, and so as to output light inputted from the scanning portion 51, to the light receiving portion 17. Lights emitted from the solid-state light sources 11a and 11b are inputted to the scanning portion 51 via the wavelength-selective light branching element 14 and the half mirror 61, and are radiated to a target so as to scan the target. Scattered light returned from the target to the scanning portion 51 is reflected by the scanning portion 51 and the half mirror 61 and then detected by the light receiving portion 17.

As described above, according to the spectroscopic apparatus 60 of the sixth embodiment, the field of view of the light receiving portion 17 follows a direction in which light scans by the scanning portion 51. Therefore, it becomes possible to reduce change in the light reception amount due to influence of the scanning angle.

In addition, since the light receiving portion 17 can be placed at the same side as the solid-state light sources 11a and 11b, the size of the spectroscopic apparatus 60 can be reduced.

It is noted that, as the configuration in which the light receiving portion 17 is placed at the same side as the solid-state light sources 11a and 11b, instead of using the half mirror 61, the polarization beam splitter, the half mirror and the holed lens, or the parabolic mirror described in the second, third, and fourth embodiments may be used. In the case of using the holed lens or the parabolic mirror, light scattered from a target and reflected by the scanning portion 51 can be received over a wide range, thus obtaining an effect of increasing the light reception amount.

Seventh Embodiment

Figure 13:
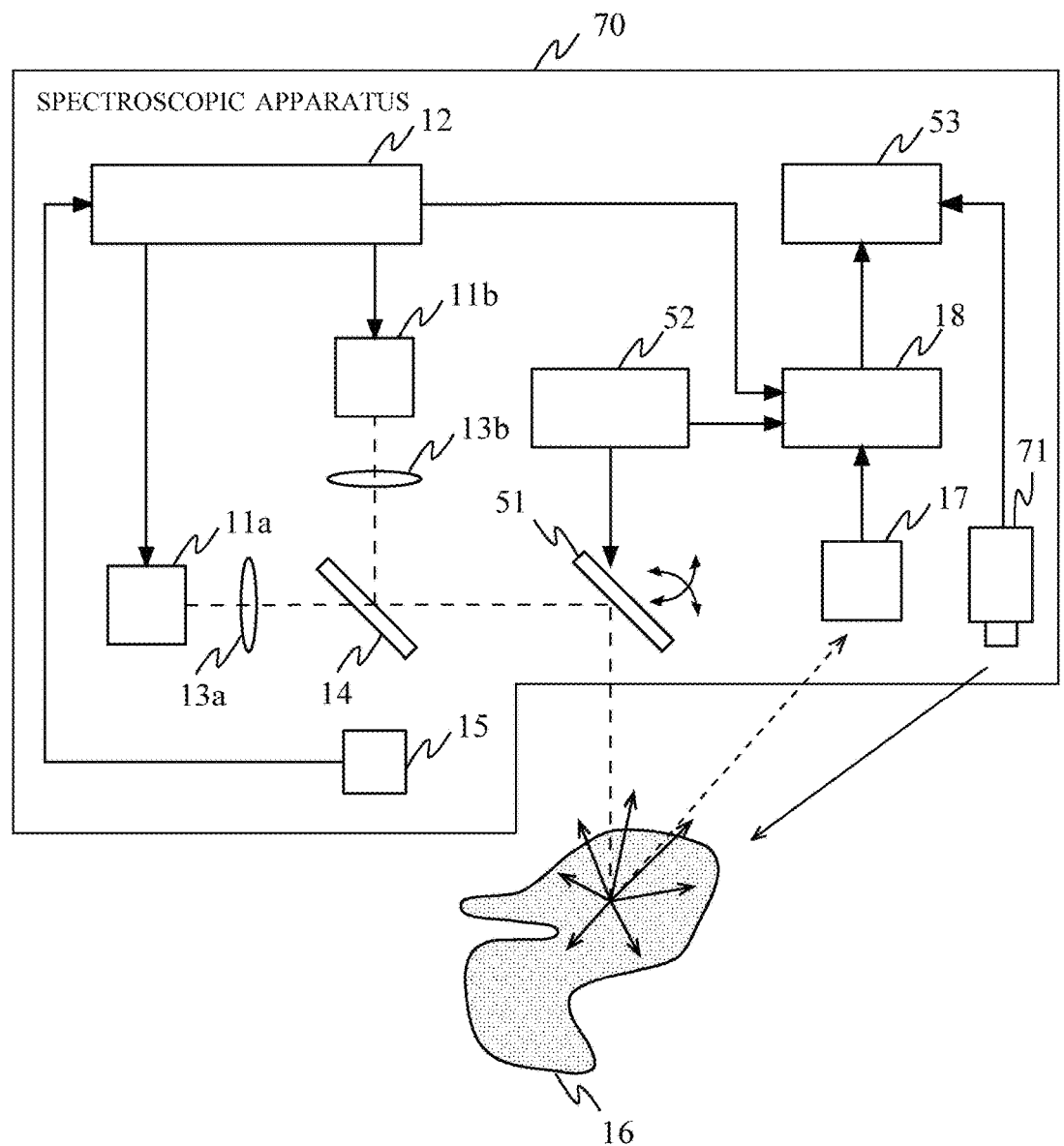
FIG. 13 is a configuration diagram of a spectroscopic apparatus 70 according to the seventh embodiment.

FIG. 13 is a configuration diagram of a spectroscopic apparatus 70 according to the seventh embodiment. The spectroscopic apparatus 70 includes the solid-state light sources 11a and 11b, the light source control portion 12, the lenses 13a and 13b, the wavelength-selective light branching element 14, the front light monitor 15, the light receiving portion 17, the measuring portion 18, the scanning portion 51, the scan driving portion 52, the output portion 53, and a camera 71.

The spectroscopic apparatus 70 is different from the spectroscopic apparatus 60 in that the camera 71 is provided. Hereinafter, the different part will be described. The same components other than this are denoted by the same reference characters, and the description thereof is omitted.

The camera 71 is an imaging device having a sensitivity in a wavelength band from 0.3 μm to 1.0 μm, and is placed so as to be able to image the entirety or a part of a target. As an imaging device used for the camera 71, an imaging device such as a CCD or CMOS using silicon may be used.

In the case where an object 16 is "water", for the wavelength $\lambda 1$ of light emitted from the solid-state light source 11a, a wavelength in the vicinity of 1.45 μm which is an absorption peak of water, or preferably, a wavelength of 1.2 μm or longer is used. On the other hand, for the wavelength $\lambda 2$ of light emitted from the solid-state light source 11b, a wavelength of 0.3 μm to 1.0 μm for which the camera 71 has a sensitivity is used. Thus, the position where water is present can be detected by using the lights with wavelengths $\lambda 1$ and $\lambda 2$, and further, a real image of the target can be taken by using the light with wavelength $\lambda 2$. For example, if a semiconductor laser with a wavelength of 1.3 μm or 1.55 μm is used for the solid-state light source 11a, and a semiconductor laser with a wavelength of 0.78 μm is used for the solid-state light source 11b, the ratio in absorption coefficient between the light with wavelength λ1 and the light with wavelength λ2 for water can be set at about two times or greater.

As described above, according to the spectroscopic apparatus 70 of the seventh embodiment, it becomes possible to display, on the output portion 53, a distribution image of an object 16 (for example, water) so as to be superimposed on a visible-light image of a target surface taken by the camera 71. As a result, it becomes possible to perform the display so that an observer can easily recognize where the object 16 is present in the target.

In addition, since a wavelength for which the camera 71 has an sensitivity is used as the wavelength λ2, an effect of facilitating position adjustment in superimposing a distribution image of an object 16 on a visible-light image of a target surface taken by the camera 71 is also obtained. Further, if a wavelength (for example, 0.7 μm or longer) of invisible light for which a human's eye does not have a sensitivity is selected as the wavelength λ2, it becomes possible to, even when there is a person at a target, obtain a distribution of an object 16 without attracting the person's attention or surprising the person.

In the case where an object 16 is "water", the spectroscopic apparatus 70 of the seventh embodiment can be utilized and applied in various situations. For example, it can be assumed that there is a floor as a target, on which a person walks, and water spilled on the floor surface is detected. In such a situation, the location of the spilled water on the floor surface is specified, and an image of the detected water is displayed on the output portion 53 so as to be superimposed on an image of the floor surface, whereby an observer of the output portion 53 is notified of presence or absence of water and its position. This enables the observer to, for example, take measures for preventing a person from slipping at the location where water has spilled. In addition, for example, when water is detected, an alarm may be issued to notify an observer, or a position where water is leaked may be reported to a cleaning robot so that the cleaning robot automatically cleans the floor. In this case, as the cleaning position, the entire area (target) monitored by the spectroscopic apparatus 70 may be reported or a part including the water leaked position may be reported.

Hereinafter, several application examples of the spectroscopic apparatus 70 will be further described.

Application Example 1

Figure 14:
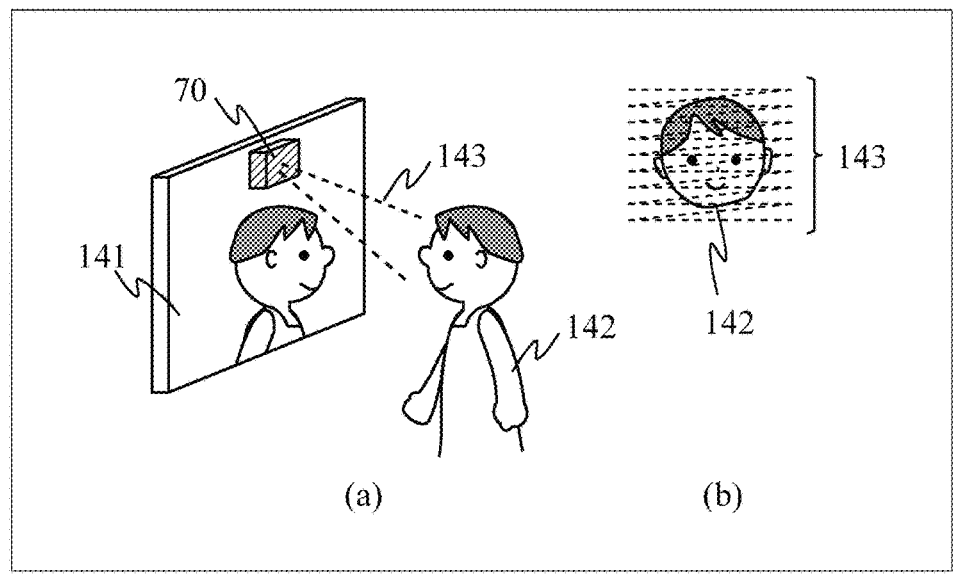
FIG. 14 is a diagram for explaining an application example 1 of the spectroscopic apparatus 70.

FIG. 14 is a diagram for explaining an application example 1 of the spectroscopic apparatus 70. In the application example 1 in FIG. 14, the spectroscopic apparatus 70 is provided at an upper portion of a display 141. The display 141 is a display device having a function of displaying information acquired by the spectroscopic apparatus 70, as an image.

As shown in (a) of FIG. 14, the spectroscopic apparatus 70 2-dimensionally scans the face of a user 142 standing in front of the display 141, to detect a position where water is present in the skin surface, and takes the face of the user 142 with a camera 71. (b) of FIG. 14 is a diagram schematically showing the way of 2-dimensionally scanning the face of the user 142 with a scan beam 143. The spectroscopic apparatus 70 displays the detected position where water is present, so as to be superimposed on the taken face image, on the display 141. On the display 141, simply, only a part where water is present and a part where no water is present may be displayed, or a difference in the ratio of scattered light with wavelength λ1 and scattered light with wavelength λ2, which occurs due to difference in water amount, may be displayed as a gradation image, whereby a part where there is much water and a part where there is little water may also be displayed.

According to the configuration of the application example 1, since a water amount distribution in the face of a user 142 can be obtained, it is possible to, for example, confirm the effect of cosmetics or confirm a health condition. It is noted that a measurement target is not limited to the face of a user 142, but a water amount distribution of each part of a body may be measured.

The spectroscopic apparatus 70 and the display 141 may be placed separately from each other. For example, the spectroscopic apparatus 70 may be placed near a door or in a bathroom, and the display 141 may be placed in a living room. In addition, if a water distribution measured by the spectroscopic apparatus 70 is accumulated in a storage device (not shown), a change history can be displayed on the display 141. In this case, for example, 2-dimensional images may be displayed so as to be arranged in chronological order, or a change history of the water amount only at any one point of a skin, for example, the center of a forehead, may be displayed as a graph. Thus, since the display 141 and the spectroscopic apparatus 70 are separated, restriction on measurement place can be reduced, and a change history of a skin condition can be easily known.

Application Example 2

Figure 15:
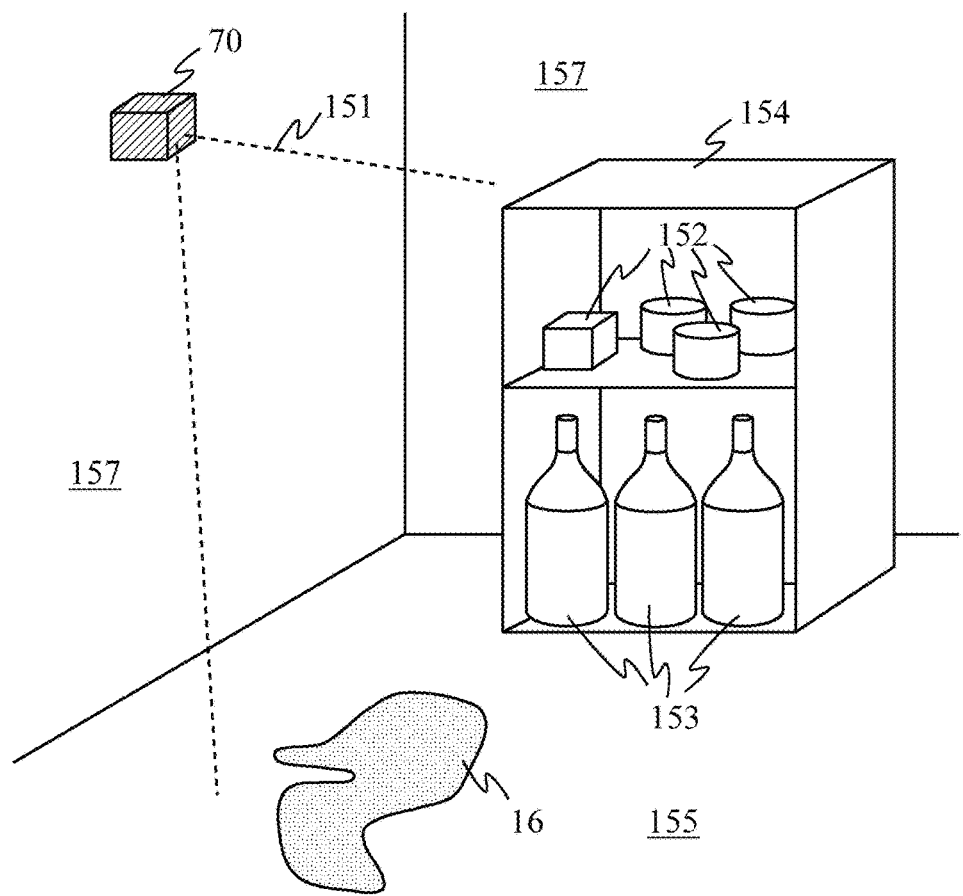
FIG. 15 is a diagram for explaining an application example 2 of the spectroscopic apparatus 70.

FIG. 15 is a diagram for explaining an application example 2 of the spectroscopic apparatus 70. In the application example 2 in FIG. 15, the spectroscopic apparatus 70 is provided at an upper portion of a wall surface 157. In a shelve 154 placed on a floor surface 155, non-liquid containers 152 and liquid containers 153 are arranged. An object 16 is liquid present on the floor surface 155, for example, spilled water.

The spectroscopic apparatus 70 2-dimensionally scans (a scan beam 151 is schematically shown) a space formed by the wall surface 157 and the floor surface 155 including the shelve 154, to detect a part where an object 16 such as water is present, and takes the space with the camera 71. Here, the output portion 53 of the spectroscopic apparatus 70 has a mask function to perform mask processing such as changing the color of a part of a displayed image, surrounding the part with a frame, decreasing the brightness thereof, or not displaying the part in accordance with an operation by an observer or the like.

According to the configuration of the application example 2, by mask processing, an area where the liquid containers 153 are arranged can be set as an area (non processing target area) that should be excluded from a range for which spectroscopic processing is to be performed, whereby, even if there is water in the liquid containers 153, it becomes easy to bring an observer's attention only to an object 16 that should be originally detected, that is, spilled water, without detecting water in the liquid containers 153. In addition, if an object 16 is detected in a non processing target area for which mask processing has not been performed, the spectroscopic apparatus 70 may automatically issue an alarm, whereby work of an observer can be reduced.

Application Example 3

Figure 16:
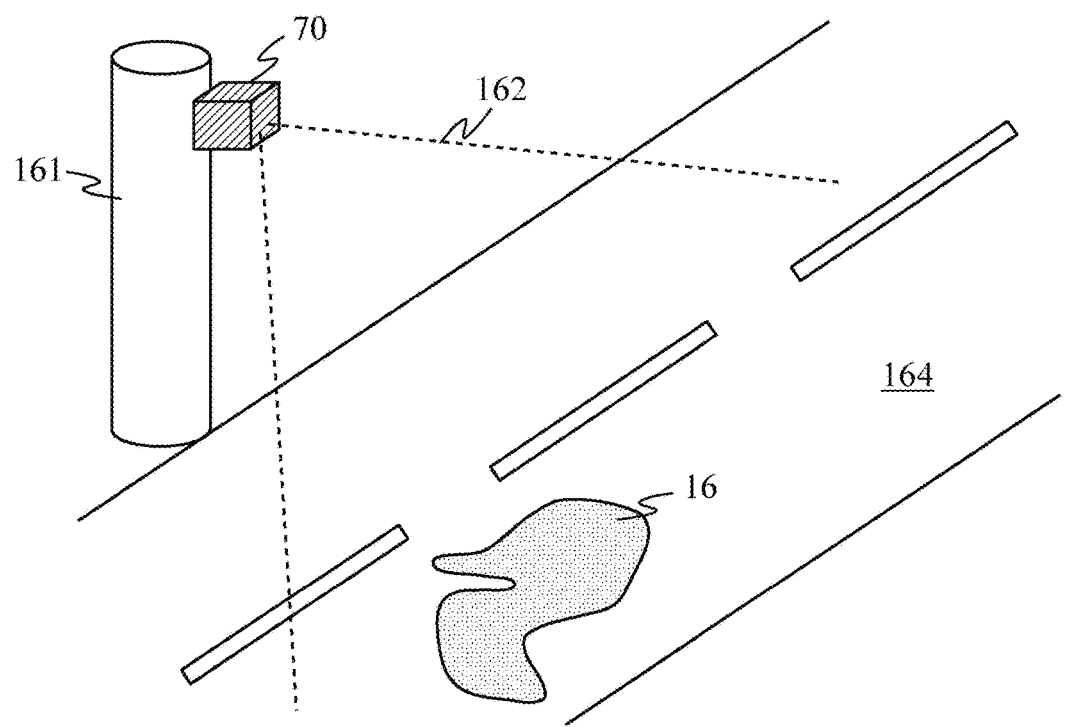
FIG. 16 is a diagram for explaining an application example 3 of the spectroscopic apparatus 70.

FIG. 16 is a diagram for explaining an application example 3 of the spectroscopic apparatus 70. In the application example 3 in FIG. 16, the spectroscopic apparatus 70 is provided at an upper portion of a pole 161 placed at the periphery of a road 164. An object 16 is a material present on the road 164, such as water generated by rainfall, spring, or the like, or spilled oil, for example.

The spectroscopic apparatus 70 2-dimensionally scans the road 164 (a scan beam 162 is schematically shown), to detect a part where an object 16 such as water or oil is present, and takes the road 164 with the camera 71.

According to the configuration of the application example 3, since an object 16 such as water or oil on the road 164 around the pole 161 can be detected by the spectroscopic apparatus 70 provided on the pole 161, it is possible to swiftly detect presence of the object 16 which obstructs normal traffic. In the case of detecting oil, for example, a wavelength in the vicinity of 3.6 μm may be used as the wavelength λ1 of light emitted by the solid-state light source 11*a*.

Application Example 4

Figure 17:
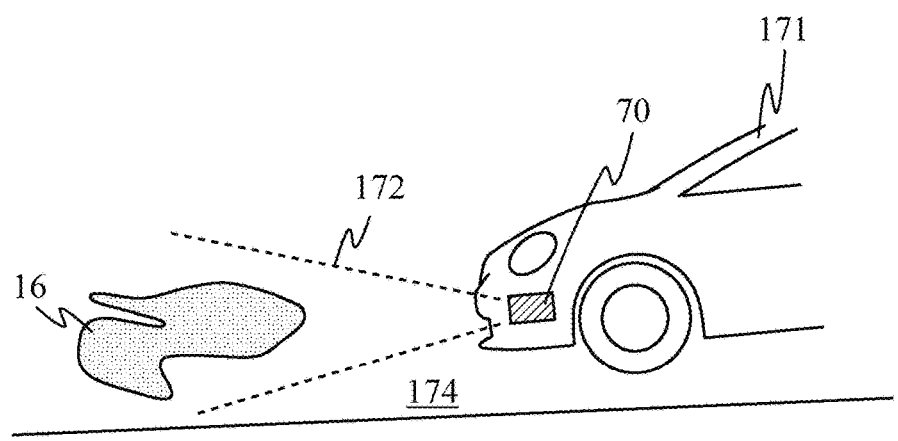
FIG. 17 is a diagram for explaining an application example 4 of the spectroscopic apparatus 70.

FIG. 17 is a diagram for explaining an application example 4 of the spectroscopic apparatus 70. In the application example 4 in FIG. 17, the spectroscopic apparatus 70 is attached at a front portion of a vehicle 171. An object 16 is a material present on a road 174, such as spring water, spilled oil, or ice due to freezing, for example.

The spectroscopic apparatus 70 2-dimensionally scans the road 174 (a scan beam 172 is schematically shown), to detect a part where an object 16 such as water or oil is present, and takes the road 174 with the camera 71. Normally, the vehicle 171 travels forward, so scan in the travelling direction can be performed as the vehicle 171 travels. Therefore, the spectroscopic apparatus 70 may perform scanning 1-dimensionally in a direction perpendicular to the vehicle travelling direction.

According to the configuration of the application example 4, since detection for an object 16 such as water, ice, or oil on the road 174 on which the vehicle 171 travels can be always performed by the spectroscopic apparatus 70 provided on the vehicle 171, it is possible to swiftly detect presence of an object 16 which obstructs normal traffic. In addition, since the spectroscopic apparatus 70 is attached to the vehicle 171 itself, it is possible to swiftly detect an object 16 present in front of the vehicle also in various places other than the road 174.

When water becomes ice with decrease in its temperature, a light absorption peak shifts toward the longer wavelength side. Therefore, for example, in the case where there is an absorption peak at 1.45 μm, with regard to light with a wavelength of 1.3 μm at a shorter wavelength side and light with a wavelength of 1.5 μm at a longer wavelength side, a light absorption amount by ice for light with a wavelength of 1.3 μm decreases (scattered light amount increases) as compared to water, and a light absorption amount by ice for light with a wavelength of 1.5 μm increases (scattered light amount decreases). Therefore, it is possible to determine which of water or ice an object 16 is, based on whether or not the ratio of the reception amount of light with a wavelength of 1.3 μm with respect to the reception amount of light with a wavelength of 1.5 μm is equal to or smaller than a predetermined threshold value. Temperature-related change in the absorption amount by water for light with a wavelength of 1.3 μm or shorter is one digit or more smaller than temperature-related change in the absorption amount by water for light with a wavelength of 1.5 μm. Therefore, it is also possible to determine which of water or ice an object 16 is, based on whether or not the ratio of the reception amount of light with a wavelength of 1.3 μm or shorter (for example, 0.98 μm or 0.78 μm) with respect to the reception amount of light with a wavelength of 1.5 μm is equal to or smaller than a predetermined threshold value. It is noted that, for change in the light reception amount (scattered light amount) by a material other than water and ice on the road 174, it is also possible to correct the light reception amount by combining measurement by light with a wavelength for which an absorption amount by water is small.

Here, change in the light absorption amount by an object 16 due to temperature change will be considered.

It is assumed that the wavelengths λ1 and λ2 are selected such that the temperature-related change amount of an absorptivity of light with wavelength λ1 for the object 16 is about ten times or more larger than the temperature-related change amount of an absorptivity of light with wavelength λ2 for the object 16. For example, in the case where the object 16 is water, 1.55 μm may be used as the wavelength λ1, and 0.98 μm may be used as the wavelength λ2. When the temperature changes by 49 degrees from 14° C. to 63° C., light absorbance of water with a thickness of 1 mm decreases by 0.15 for the wavelength of 1.55 μm, but changes by no more than 0.01 for the wavelength of 0.98 μm.

Figure 18:
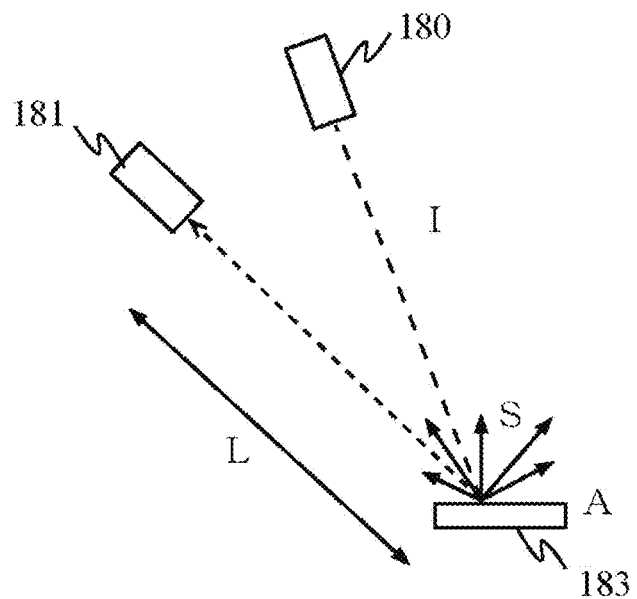
FIG. 18 is a diagram showing a scene in which radiated light is reflected and scattered by an object and then received.

As shown in FIG. 18, a model is assumed in which light with wavelength λ is radiated from a light source portion 180 to an object 183, and light reflected and scattered by the object 183 is received by the light receiving portion 181. In the case where the intensity of the light with wavelength λ radiated to the object 183 is denoted by $I_\lambda$, a scattering reflection coefficient at the object 183 is denoted by S, a light absorbance in absorption of the light with wavelength λ by the object 183 is denoted by $A_\lambda$, and the distance from the object 183 to the light receiving portion 181 is denoted by L, an intensity (reflected light amount) $D_{1.55}$ of the reflected light with the wavelength of 1.55 μm detected by the light receiving portion 181 and an intensity (reflected light amount) $D_{0.98}$ of the reflected light with the wavelength of 0.98 μm detected by the light receiving portion 181 are represented by the following expressions [2] and [3].

[Mathematical 2]

$$D_{1.55} \propto \frac{1}{L^2} S I_{1.55} 10^{-A_{1.55}} \quad [2]$$

[Mathematical 3]

$$D_{0.98} \propto \frac{1}{L^2} S I_{0.98} 10^{-A_{0.98}} \quad [3]$$

Therefore, a light reception intensity ratio $D_{1.55}/D_{0.98}$ is represented by the following expression [4].

[Mathematial 4]

$$\frac{D_{1.55}}{D_{0.98}} = \frac{I_{1.55}}{I_{0.98}} \times 10^{(A_{0.98} - A_{1.55})} \quad [4]$$

In the above expression [4], in the case where temperature-related change amounts of light absorbance for respective wavelengths are denoted by $\Delta A_{1.55}$ and $\Delta A_{0.98}$, the light reception intensity ratio when the temperature chances is represented by the following expression [5].

[Mathematical 5]

$$\frac{D_{1.55}}{D_{0.98}} = \frac{I_{1.55}}{I_{0.98}} \times 10^{A_{0.98}} \times 10^{-(A_{1.55}+\Delta A_{1.55})} \quad [5]$$
$$= C \times 10^{-\Delta A_{1.55}}$$
$$= C \times \left(1 - \Delta A_{1.55} \times \log 10 + \frac{(-\Delta A_{1.55} \times \log 10)^2}{2} + \ldots\right)$$

In the expression [5], since $\Delta A_{0.98}$ is sufficiently smaller than $\Delta A_{1.55}$ as described above, $\Delta A_{0.98}$ is neglected. In addition, a constant value part is denoted by C. From the expression [5], since the third and subsequent terms at the right hand side in the expression [5] can be neglected as long as $\Delta A_{1.55}$ is about 0.1, the light reception intensity ratio and $\Delta A_{1.55}$, e.g., a water temperature, change almost linearly. Therefore, if change in the light reception intensity ratio is known, it is possible to know change in the temperature of water which is the object 183.

As in the example of water, if the temperature-related change amount of an absorptivity for an object 16 differs by, for example, ten times or more between the wavelength λ1 and the wavelength λ2, change in the temperature of the object 16 is sufficiently figured out from the light reception intensity ratio as described above. In the case of water, the wavelengths are not limited to the above, but a wavelength of 1.4 μm or longer may be selected as λ1 and a wavelength of 1.3 μm or shorter may be selected as λ2 as appropriate, whereby the ratio of temperature-related change amounts of absorptivities of the respective wavelengths can be set at ten times or more.

It is noted that the light reception intensity of light with a wavelength of 1.55 μm is approximately linearly influenced by the temperature of water, and is exponentially influenced by the amount of water. On the other hand, the light reception intensity of light with a wavelength of 0.98 μm is not greatly influenced by the temperature of water, but is exponentially influenced by the amount of water, and decreases with increase in the amount of water. Therefore, increase or decrease in water can be determined from change in the light reception intensity of light with a wavelength of 0.98 μm. Further, by combination with water distribution data obtained by scan of light with a wavelength of 0.98 μm, a distribution of increase and decrease in water can also be figured out. In addition, after change in the amount of water is estimated from change in the light reception intensity of light with a wavelength of 0.98 μm, the amount of change in the light reception intensity of light with a wavelength of 1.55 μm due to water amount change can be calculated from the estimated water amount change. In the case where an absorption coefficient at a wavelength of 0.98 μm is denoted by α, an absorption coefficient at a wavelength of 1.55 μm is denoted by β, and change in the thickness of water through which light transmits is denoted by Δt, the light reception intensity for absorption at a wavelength of 0.98 μm differs by exp(-αΔt) times between before and after the change, and therefore Δt can be calculated from a light reception intensity ratio. For absorption at a wavelength of 1.55 μm, change in the light reception intensity due to the water thickness change is exp(-βΔt) times. Therefore, by dividing the light reception intensity change due to both water thickness change and temperature change by the light reception intensity change due to only water thickness change, only water temperature change can be figured out. Therefore, from two light reception intensity changes for a wavelength at which the light reception intensity is not greatly influenced by temperature change and a wavelength at which the light reception intensity is influenced by temperature change, water thickness change, i.e., change in water amount, and water temperature change can be respectively figured out.

Figure 19:
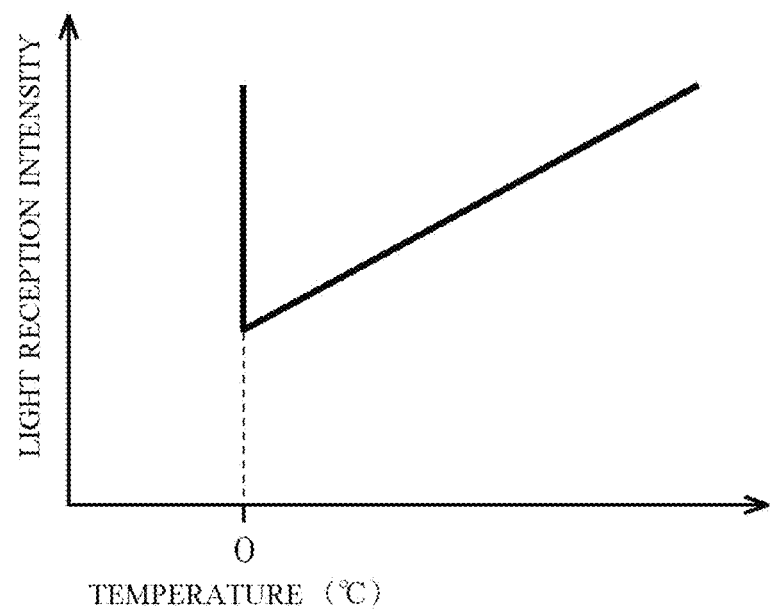
FIG. 19 is a graph showing a relationship between a water temperature and a light reception intensity.

FIG. 19 shows an experimental example in which the relationship between the water temperature and the light reception intensity of light with a wavelength of 1.55 μm is confirmed. As shown in FIG. 19, since absorption increases as the water temperature decreases, the light reception intensity of light with a wavelength of 1.55 μm decreases with decrease in the water temperature. However, when the water temperature becomes equal to or lower than 0° C. and the water freezes, the water surface becomes coarse to increase scattering, resulting in increase in the light reception intensity. Therefore, if sharp increase in the light reception intensity of light with a wavelength of 1.55 μm is detected after decrease thereof, freezing of water can be detected. Although influence of change in water amount and influence of change in temperature cannot be separated from each other with use of light with a wavelength of 1.55 μm alone, it is possible to determine only influence of temperature by also measuring the light reception intensity of light with a wavelength of 0.98 μm as described above. Thus, by using two wavelengths, detection of freezing can be performed with less erroneous detection.

Application Example 5

Figure 20:
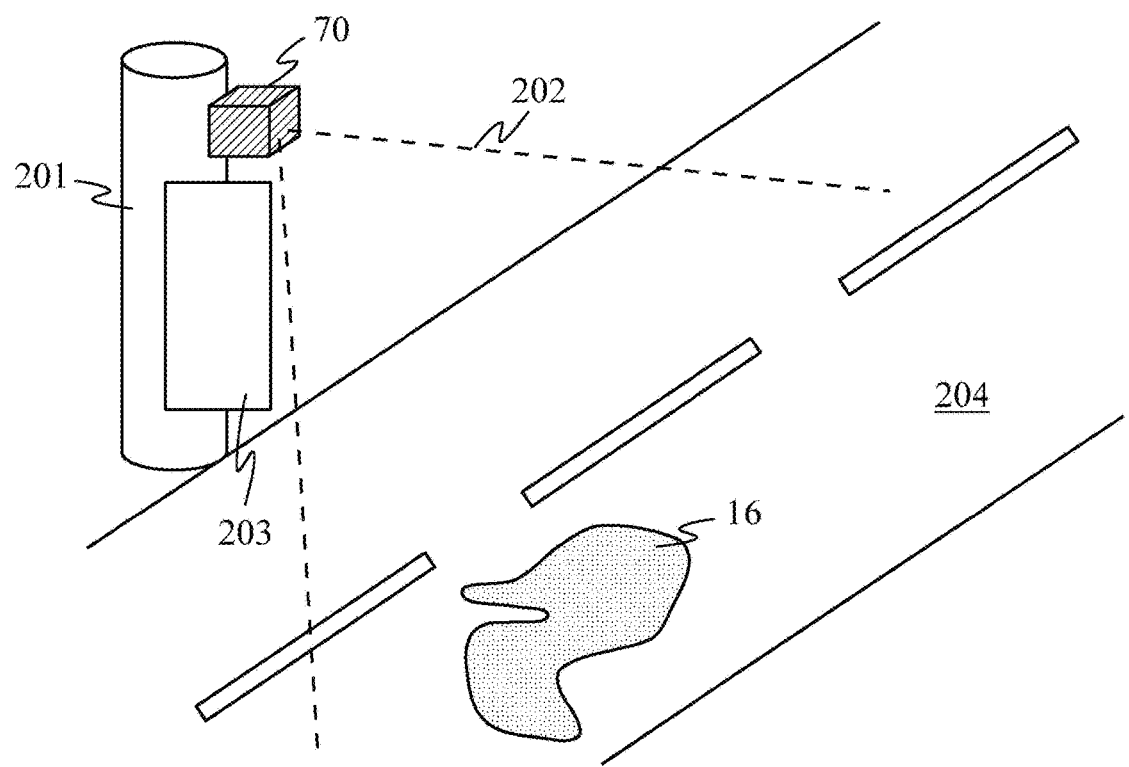
FIG. 20 is a diagram for explaining an application example 5 of the spectroscopic apparatus 70.

FIG. 20 is a diagram for explaining an application example 5 of the spectroscopic apparatus 70. In the application example 5 in FIG. 20, the spectroscopic apparatus 70 is provided at an upper portion of a pole 201 placed at the periphery of a road 204. A display 203 is a display device having a function of displaying information acquired by the spectroscopic apparatus 70 by an image, a text, or the like. An object 16 is a material present on the road 204, such as water generated by rainfall, spring, or the like, or spilled oil, for example.

The spectroscopic apparatus 70 2-dimensionally scans the road 204 (a scan beam 202 is schematically shown), to detect a part where an object 16 such as water or oil is present, and takes the road 204 with the camera 71. The spectroscopic apparatus 70 causes the display 203 to display information about the detected object 16 or the taken road 204. In addition, the spectroscopic apparatus 70 can transmit such information to a vehicle or a pedestrian therearound, a road administrator, or the like via a communication means (not shown).

According to the configuration of the application example 5, the spectroscopic apparatus 70 provided on the pole 201 can detect the distribution, temperature, and freezing of water on the road 204 around the pole 201 and display such information to a vehicle or a pedestrian therearound by the display 203, whereby dangers such as skidding accident can be decreased. In addition, the information can be transmitted via a communication means also to a pedestrian, a vehicle, or a road administrator present at a place where they cannot directly view the display, whereby security is ensured further effectively.

The technique of the application example 5 can be used for, besides water on the road 204, various applications such as detection or display of water distribution or water temperature for water spilled on an indoor floor, indoor condensation, a washing process or a drying process in a factory, or detection or display of freezing in a cooling facility.

Eighth Embodiment

Figure 21:
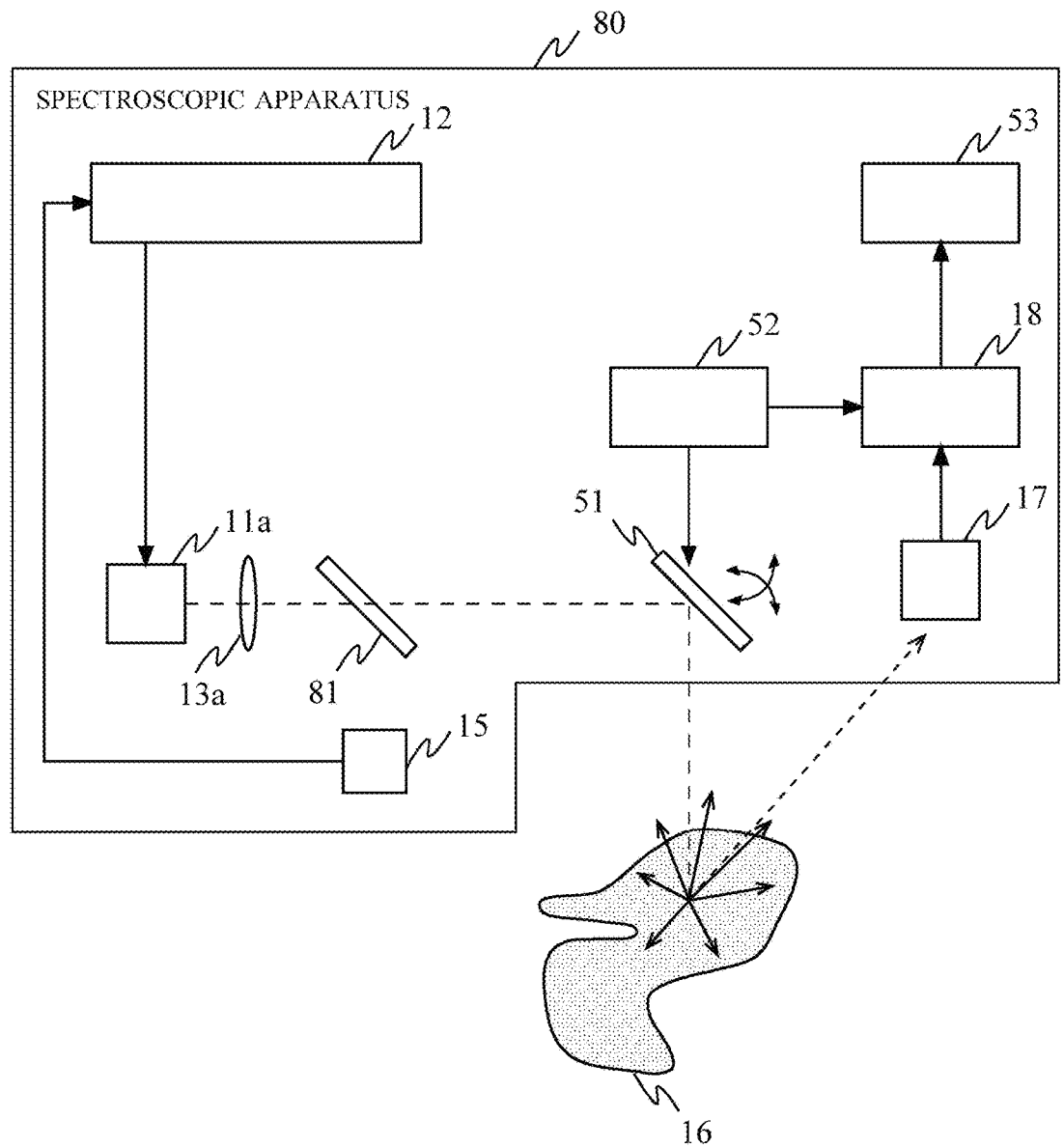
FIG. 21 is a configuration diagram of a spectroscopic apparatus 80 according to the eighth embodiment.

FIG. 21 is a configuration diagram of a spectroscopic apparatus 80 according to the eighth embodiment. The spectroscopic apparatus 80 includes the solid-state light source 11a, the light source control portion 12, the lens 13a, the wavelength-selective light branching element 14, the front light monitor 15, the light receiving portion 17, the measuring portion 18, the scanning portion 51, the scan driving portion 52, the output portion 53, and a beam sampler 81.

The spectroscopic apparatus 80 is different from the spectroscopic apparatus 50 in that the solid-state light source 11b and the lens 13b are removed and the beam sampler 81 is provided. Hereinafter, the different part will be described. The same components other than this are denoted by the same reference characters, and the description thereof is omitted.

The beam sampler 81 reflects a part of light emitted from the solid-state light source 11a, to cause the part of light to enter the front light monitor 15. Output of the front light monitor 15 is inputted to the light source control portion 12 to perform feedback so that output of the solid-state light source 11a has a constant value.

In the spectroscopic apparatus 80, the number of solid-state light sources is one unlike the configurations of the spectroscopic apparatuses 10 to 70 described above. Therefore, the spectroscopic apparatus 80 performs at least two cycles of scanning by the solid-state light source 11a, thereby detecting temporal change in a target and detecting whether or not an object 16 is present. In the following description, a scan cycle performed first is referred to as a "first scan cycle" and the next (or subsequent) scan cycle is referred to as a "second scan cycle".

First, in the first scan cycle, while the scanning portion 51 causes light to scan a target, the intensity of light received by the light receiving portion 17 which has been reflected and scattered by the target is stored, for each scan position, as a light reception amount in the measuring portion 18. Specifically, when no object 16 is present at a target, the first scan cycle is executed to store a light reception amount in the target surface, as initial data.

Next, in the second scan cycle, while the scanning portion 51 causes light to scan the target, the intensity of light received by the light receiving portion 17 which has been reflected and scattered by the target is compared with the light reception amount at the same scan position, stored in the measuring portion 18 in the first scan cycle. A result of the comparison, e.g., a ratio of light reception amounts, is displayed as 2-dimensional gradation on the output portion 53.

As described above, according to the spectroscopic apparatus 80 of the eighth embodiment, it is possible to detect whether or not an object 16 is present and obtain a 2-dimensional distribution thereof by repeating the second scan cycle. In addition, since the beam sampler 81 is employed to keep output of the solid-state light source 11a constant, it is possible to confirm temporal change in a target through a plurality of scan cycles, and it is possible to detect whether or not an object 16 is present even by a single solid-state light source 11a.

It is preferable that the first scan cycle is periodically performed, for example, once every hour or once every day, to correct influence due to change factors other than an object 16 as appropriate.

As a storage location of a light reception amount for each scan position, instead of the measuring portion 18, a storage portion connected to a network may be used. By separating a storage portion and a measuring portion, one storage portion can be shared by a plurality of spectroscopic apparatuses connected to the network, whereby system maintenance can be facilitated and the cost can be reduced.

Ninth Embodiment

Figure 22:
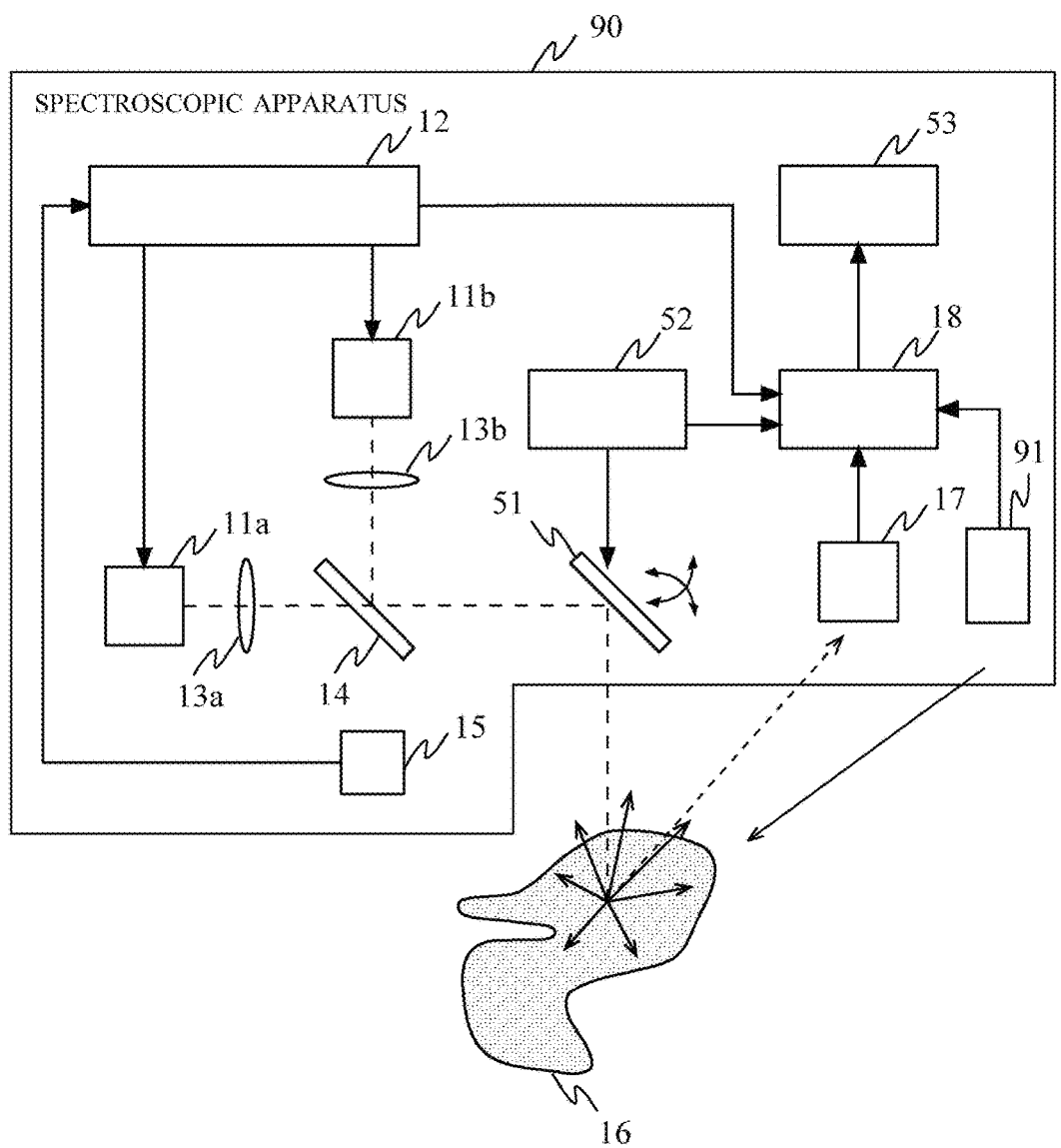
FIG. 22 is a configuration diagram of a spectroscopic apparatus 90 according to the ninth embodiment.

FIG. 22 is a configuration diagram of a spectroscopic apparatus 90 according to the ninth embodiment. The spectroscopic apparatus 90 includes the solid-state light sources 11a and 11b, the light source control portion 12, the lenses 13a and 13b, the wavelength-selective light branching element 14, the front light monitor 15, the light receiving portion 17, the measuring portion 18, the scanning portion 51, the scan driving portion 52, the output portion 53, and a distance measuring portion 91.

The spectroscopic apparatus 90 is different from the spectroscopic apparatus 50 in that the distance measuring portion 91 is provided. Hereinafter, the different part will be described. The same components other than this are denoted by the same reference characters, and the description thereof is omitted.

The distance measuring portion 91 measures the distance between the spectroscopic apparatus 90 and a target by a known method called a light flight time measurement method or a time-of-flight method. To briefly describe, the light flight time measurement method is a method of calculating a distance by measuring a time from emission of light until the light is reflected by a measurement target and returns. Specifically, the distance measuring portion 91 measures a time until light emitted from the solid-state light source 11a (or the solid-state light source 11b) is reflected by a target and arrives at the light receiving portion 17, and thereby calculates the distance between the spectroscopic apparatus 90 and the target. In FIG. 22, for facilitating understanding, the case where the distance measuring portion 91 is provided separately from the measuring portion 18 is shown, but the distance measuring portion 91 may be included in the measuring portion 18.

As described above, according to the spectroscopic apparatus 90 of the ninth embodiment, it is possible to measure a 3-dimensional shape of a target, using the distance measuring portion 91. Thus, a surface that is horizontal or vertical to a ground surface can be extracted from the 3-dimensional shape of the target. Therefore, for example, among such horizontal surfaces, a horizontal surface at the lowest position can be considered to be a floor, whereby only water present on the floor can be extracted, or a vertical surface can be considered to be a wall surface, whereby only condensation on the wall surface can be extracted.

It is noted that, in order to extract a horizontal surface or a vertical surface from a 3-dimensional shape, it is necessary to know the orientation of the spectroscopic apparatus 90 itself. Regarding this, the spectroscopic apparatus 90 may be provided with a level, or orientation data may be stored in the measuring portion 18 when the spectroscopic apparatus 90 is installed.

Tenth Embodiment

Figure 23:
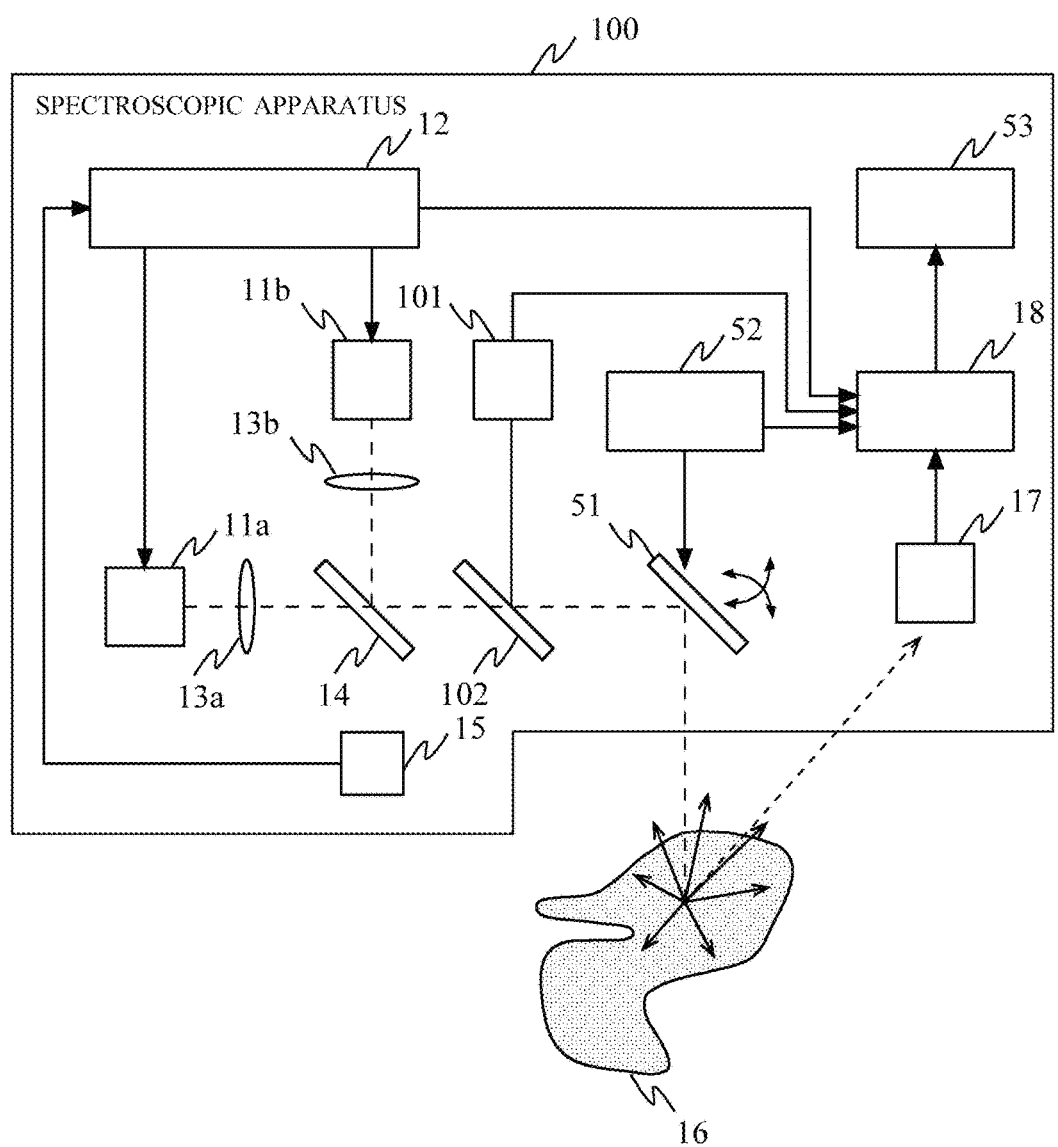
FIG. 23 is a configuration diagram of a spectroscopic apparatus 100 according to the tenth embodiment.

FIG. 23 is a configuration diagram of a spectroscopic apparatus 100 according to the tenth embodiment. The spectroscopic apparatus 100 includes the solid-state light sources 11a and 11b, the light source control portion 12, the lenses 13a and 13b, the wavelength-selective light branching element 14, the front light monitor 15, the light receiving portion 17, the measuring portion 18, the scanning portion 51, the scan driving portion 52, the output portion 53, a non-contact temperature measuring portion 101, and a wavelength-selective mirror 102.

The spectroscopic apparatus 100 is different from the spectroscopic apparatus 50 in that the non-contact temperature measuring portion 101 and the wavelength-selective mirror 102 are provided. Hereinafter, the different part will be described. The same components other than this are denoted by the same reference characters, and the description thereof is omitted.

The non-contact temperature measuring portion 101 detects an infrared ray radiated from a target or an object 16, and measures a temperature. As the non-contact temperature measuring portion 101, for example, a radiation thermometer using a middle infrared ray or a far infrared ray may be used. The wavelength-selective mirror 102 reflects light with a wavelength that is used by the non-contact temperature measuring portion 101, and transmits light with a wavelength of emission from the solid-state light sources 11a and 11b. The scanning portion 51 reflects not only light with a wavelength of emission from the solid-state light sources 11a and 11b, but also light with a wavelength that is used by the non-contact temperature measuring portion 101. In the measuring portion 18, data of temperature characteristics of light absorption by an object 16 is stored. Among scattered lights returning from a target to the scanning portion 51, light (an infrared ray, a middle infrared ray, a far infrared ray) with a wavelength that is used by the non-contact temperature measuring portion 101 is reflected by the scanning portion 51 and the wavelength-selective mirror 102, to be detected by the non-contact temperature measuring portion 101. Thus, the temperature at the scanned position can be measured.

As described above, according to the spectroscopic apparatus 100 of the tenth embodiment, since a temperature T (K) at a scanned position can be determined, whether or not an object 16 is present can be determined using a ratio between absorptivity of light from the solid-state light source 11a and absorptivity of light from the solid-state light source 11b at the temperature T (K), obtained from the temperature characteristics of light absorption by the object 16 stored in advance in the measuring portion 18, whereby spectroscopic processing with high accuracy that is less influenced by temperature can be performed. That is, it is possible to perform spectroscopic processing appropriately based on a light reception amount corrected by an amount corresponding to change in temperature. The present embodiment is particularly effective to such an application example in which a target varies every moment, for example, for improvement in accuracy of the spectroscopic apparatus 70 mounted on the vehicle 171 as in the application example 4 of the spectroscopic apparatus 70 according to the seventh embodiment. Even in the case where a target is stationary, the present embodiment is effective for improvement in accuracy of the spectroscopic apparatus at such a place with great temperature unevenness.

In the tenth embodiment, the configuration in which the non-contact temperature measuring portion 101 detects light returning from a target via the scanning portion 51 for each scan point has been described. However, a configuration in which light directly returning from a target is detected may be used. In this case, by using a radiation thermometer of area-sensor type, the temperature of a target can be determined for each minute area thereof. Alternatively, even by a radiation thermometer of line-sensor type or spot-type, since the average temperature of a target can be used as a correction value, accuracy of spectroscopic processing is improved.

Thus, spectroscopic apparatuses according to one or a plurality of aspects of the present invention have been described based on the above embodiments, but the present invention is not limited to these embodiments. Unless deviating the gist of the present invention, configurations in which various modifications conceived by a person skilled in the art are applied to these embodiments and configurations in which components in different embodiments are combined may be included in the scope of the one or a plurality of aspects of the present invention.

For example, in the above embodiments, each component may be formed by dedicated hardware, or may be realized by execution of a software program suited for each component. Each component may be realized by a program executing portion such as a CPU or a processor reading and executing such a software program stored in a storage medium such as a hard disk or a semiconductor memory.

The spectroscopic apparatus of the present invention is useful for a component analyzing device or the like that has a light source with a specified wavelength and does not use a spectroscopic device. In addition, the spectroscopic apparatus of the present invention is applicable for purposes such as detection of presence of a specific material such as water or visualization of distribution thereof.

DESCRIPTION OF THE REFERENCE CHARACTERS 10, 20, 30, 40, 50, 60, 70, 80, 90, 100 spectroscopic apparatus
11a, 11b, 180 solid-state light source (light source portion)
12 light source control portion
13a, 13b lens
14 wavelength-selective light branching element
15 front light monitor
16, 183 object
17, 181 light receiving portion
18 measuring portion
21 polarization beam splitter
31 holed lens
32, 61 half mirror
41 parabolic mirror
51 scanning portion
52 scan driving portion
53 output portion
71 camera
81 beam sampler
91 distance measuring portion
101 non-contact temperature measuring portion
102 wavelength-selective mirror
141, 203 display
142 user
143, 151, 162, 172, 202 scan beam
152, 153 container
154 shelve
155 floor surface
157 wall surface
161, 201 pole
164, 174, 204 road
171 vehicle 301 liquid leakage detecting device
302 oil sealing facility
303, 303a oil
304 middle infrared light

The invention claimed is:

1. A spectroscopic apparatus using light having a first wavelength which has a predetermined absorptivity for a specific object, and light having a second wavelength which has a smaller absorptivity for the specific object than the first wavelength, the spectroscopic apparatus comprising:
   a light radiating portion configured to radiate, to a target, collimated light with the first wavelength which is obtained by the light having the first wavelength being substantially collimated, and collimated light with the second wavelength which is obtained by the light having the second wavelength being substantially collimated;
   a light receiving portion configured to receive first scattered light obtained by the collimated light with the first wavelength transmitting through the target or being reflected by the target, and second scattered light obtained by the collimated light with the second wavelength transmitting through the target or being reflected by the target; and
   a measuring portion configured to generate information to be used for detection of the specific object at the target, based on a difference between the first scattered light and the second scattered light received by the light receiving portion,
   wherein the light radiating portion includes a scan processing portion configured to radiate the collimated light with the first wavelength directly to the target so as to scan in 2 dimensional directions by using reflection and diffraction, and then radiate the collimated light with the second wavelength directly to the target after radiating with the first wavelength so as to scan in the 2-dimensional directions by using reflection and diffraction.

2. The spectroscopic apparatus according to claim 1, wherein the light radiating portion includes:
   a first solid-state light source configured to emit the light having the first wavelength;
   a second solid-state light source configured to emit the light having the second wavelength; and
   a light source control portion configured to drive the first and second solid-state light sources so that the collimated light with the first wavelength and the collimated light with the second wavelength are received in a discriminated manner by the light receiving portion.

3. The spectroscopic apparatus according to claim 2, wherein the light source control portion drives the first solid-state light source and the second solid-state light source with emission timings thereof shifted from each other.

4. The spectroscopic apparatus according to claim 2, wherein the light source control portion drives the first solid-state light source and the second solid-state light source so as to be modulated with different frequencies.

5. The spectroscopic apparatus according to claim 2, wherein the light radiating portion further includes
   a first lens configured to output the light having the first wavelength so as to be the collimated light with the first wavelength,
   a second lens configured to output the light having the second wavelength so as to be the collimated light with the second wavelength, and
   a wavelength-selective light branching element configured to cause a path of the collimated light with the first wavelength and a path of the collimated light with the second wavelength to substantially coincide with each other.

6. The spectroscopic apparatus according to claim 5, wherein
   the first solid-state light source, the first lens, and the wavelength-selective light branching element are arranged on a first light path which is a path of the light having the first wavelength emitted from the first solid-state light source, in order of the first solid-state light source, the first lens, and then the wavelength-selective light branching element,
   the second solid-state light source, the second lens, and the wavelength-selective light branching element are arranged on a second light path which is a path of the light having the second wavelength emitted from the second solid-state light source, in order of the second solid-state light source, the second lens, and then the wavelength-selective light branching element,
   the first light path and the second light path intersect substantially perpendicularly with each other, and
   the wavelength-selective light branching element causes the collimated light with the first wavelength to transmit therethrough and reflects the collimated light with the second wavelength, thereby causing the path of the collimated light with the first wavelength and the path of the collimated light with the second wavelength to substantially coincide with each other.

7. The spectroscopic apparatus according to claim 6, wherein the light radiating portion further includes a polarization beam splitter configured to output, to the target, P-polarization-component light among the collimated light with the first wavelength and the collimated light with the second wavelength whose paths have been caused to substantially coincide with each other by the wavelength-selective light branching element.

8. The spectroscopic apparatus according to claim 7, wherein the polarization beam splitter reflects only S-polarization-component light so as to be received by the light receiving portion and does not reflect P-polarization-component light, among lights reflected from the target.

9. The spectroscopic apparatus according to claim 5, wherein the light radiating portion further includes a polarization beam splitter configured to output, to the target, P-polarization-component light among the collimated light with the first wavelength and the collimated light with the second wavelength whose paths have been caused to substantially coincide with each other by the wavelength-selective light branching element.

10. The spectroscopic apparatus according to claim 9, wherein the polarization beam splitter reflects only S-polarization-component light so as to be received by the light receiving portion and does not reflect P-polarization-component light, among lights reflected from the target.

11. The spectroscopic apparatus according to claim 1, wherein the light radiating portion radiates the collimated light with the first wavelength and the collimated light with the second wavelength to the same position on the target.

12. The spectroscopic apparatus according to claim 1, wherein the measuring portion determines whether or not the specific object is present at the target, based on a ratio between an intensity of the first scattered light received by the light receiving portion and an intensity of the second scattered light received by the light receiving portion.

13. The spectroscopic apparatus according to claim 12, wherein if the intensity of the second scattered light is greater than the intensity of the first scattered light, the measuring portion determines that the specific object is present at the target.

14. The spectroscopic apparatus according to claim 1, wherein the first wavelength is set to be equal to or longer than 1.4 μm and the second wavelength is set to be equal to or shorter than 1.3 μm so that a temperature-related change amount of absorptivity of the light having the first wavelength for the specific object is ten times or more greater than a temperature-related change amount of absorptivity of the light having the second wavelength for the specific object.

15. The spectroscopic apparatus according to claim 1, wherein the scan processing portion first scans an entirety of the target in a spatially coarse manner, and if it is determined that the specific object is present, next scans an area where the specific object is present, in a spatially dense manner.

16. The spectroscopic apparatus according to claim 1, wherein the scan processing portion first scans an entirety of the target in a temporally coarse manner, and if it is determined that the specific object is present, next scans an area where the specific object is present, in a temporally dense manner.

17. The spectroscopic apparatus according to claim 1, further comprising an output portion configured to output whether or not the specific object is present at the target, as 2-dimensional area information, based on the scanning by the scan processing portion and the information generated by the measuring portion.

18. The spectroscopic apparatus according to claim 17, further comprising a camera configured to take the target, wherein
the output portion outputs 2-dimensional area information about whether or not the specific object is present at the target, with the 2-dimensional area information superimposed on a 2-dimensional image of the target taken by the camera.

19. The spectroscopic apparatus according to claim 18, wherein the second wavelength is set to an invisible wavelength in a range of wavelengths for which the camera has sensitivity.

20. The spectroscopic apparatus according to claim 17, further comprising a distance measuring portion configured to measure a distance to the target, wherein
the output portion adds information about the distance measured by the distance measuring portion to 2-dimensional area information about whether or not the specific object is present at the target, and outputs a resultant information as 3-dimensional area information.

21. The spectroscopic apparatus according to claim 17, further comprising a temperature measuring portion configured to measure a temperature of the target, wherein
the output portion outputs 2-dimensional area information about whether or not the specific object is present at the target, with the 2-dimensional area information corrected in accordance with information about the temperature measured by the temperature measuring portion.

22. The spectroscopic apparatus according to claim 1, wherein
the specific object is water, and
the first wavelength is set to be equal to or longer than 1.4 μm and the second wavelength is set to be equal to or shorter than 1.3 μm.

* * * * *